(12) United States Patent
Wei et al.

US011976104B2

(10) Patent No.: US 11,976,104 B2
(45) Date of Patent: May 7, 2024

(54) TLR9 LIGAND TRAP

(71) Applicant: H. Lee Moffitt Cancer Center and Research Institute, Inc., Tampa, FL (US)

(72) Inventors: Sheng Wei, Tampa, FL (US); Alan F. List, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 695 days.

(21) Appl. No.: 17/181,246

(22) Filed: Feb. 22, 2021

(65) Prior Publication Data

US 2021/0253664 A1 Aug. 19, 2021

Related U.S. Application Data

(63) Continuation of application No. PCT/US2019/047706, filed on Aug. 22, 2019.

(60) Provisional application No. 62/721,832, filed on Aug. 23, 2018.

(51) Int. Cl.
*C07K 14/705* (2006.01)
*A61P 35/00* (2006.01)
*G01N 33/574* (2006.01)

(52) U.S. Cl.
CPC ............ *C07K 14/705* (2013.01); *A61P 35/00* (2018.01); *G01N 33/57407* (2013.01); *G01N 33/57488* (2013.01); *C07K 2319/30* (2013.01)

(58) Field of Classification Search
CPC .................................................. C07K 14/705
USPC ...................................................... 424/134.1
See application file for complete search history.

(56) References Cited

U.S. PATENT DOCUMENTS

| 2003/0104523 A1* | 6/2003 | Bauer ..................... A61P 37/00 435/6.16 |
| 2003/0232074 A1 | 12/2003 | Lipford et al. |
| 2009/0208501 A1 | 8/2009 | Visintin et al. |

OTHER PUBLICATIONS

International Search Report issued for PCT/US2019/047706 dated Nov. 14, 2019.

* cited by examiner

*Primary Examiner* — Sean E Aeder
(74) *Attorney, Agent, or Firm* — Thomas | Horstemeyer, LLP

(57) ABSTRACT

Myelodysplastic syndrome (MDS) hematopoietic stem and progenitor cells (HSPC) translocate endosomal Toll-Like receptor (TLR)-9 to the plasma membrane, thereby sensitizing these clonal propagating cells to respective ligands in the microenvironment. TLR9 is the cognate receptor for RNA:DNA hybrids (R-loops) and unmethylated CpG oligonucleotides in oxidized mitochondrial DNA, the latter of which is abundant in the bone marrow microenvironment as a result of massive medullary pyroptotic cytolytic cell death. Both ligands are important danger-associated molecular patterns (DAMPs) triggering innate immune activation and chronic inflammation that contributes to MDS pathogenesis. In an effort to neutralize these DAMPs and disrupt this feed-forward inflammatory cascade, a chimeric protein was designed fusing the external epitopes of TLR9 to the Fc domain of human IgG4 to serve as a decoy receptor or ligand trap recognizing extracellular RNA:DNA hybrids (R-loops) and oxidized mitochondrial DNA.

10 Claims, 37 Drawing Sheets

Specification includes a Sequence Listing.

MDS-BM treated with TLR9-IgG4 chimeric protein

SEQUENCE LISTING

```
<160> NUMBER OF SEQ ID NOS: 7

<210> SEQ ID NO 1
<211> LENGTH: 794
<212> TYPE: PRT
<213> ORGANISM: Homo sapiens

<400> SEQUENCE: 1

Met Leu Gly Thr Leu Pro Ala Phe Leu Pro Cys Glu Leu Gln Pro His
1               5                   10                  15

Gly Leu Val Asn Cys Asn Trp Leu Phe Leu Lys Ser Val Pro His Phe
            20                  25                  30

Ser Met Ala Ala Pro Arg Gly Asn Val Thr Ser Leu Ser Leu Ser Ser
        35                  40                  45
```

```
Asn Arg Ile His His Leu His Asp Ser Asp Phe Ala His Leu Pro Ser
 50                  55                  60

Leu Arg His Leu Asn Leu Lys Trp Asn Cys Pro Val Gly Leu Ser
 65                  70                  75                  80

Pro Met His Phe Pro Cys His Met Thr Ile Glu Pro Ser Thr Phe Leu
                 85                  90                  95

Ala Val Pro Thr Leu Glu Glu Leu Asn Leu Ser Tyr Asn Asn Ile Met
             100                 105                 110

Thr Val Pro Ala Leu Pro Lys Ser Leu Ile Ser Leu Ser Leu Ser His
             115                 120                 125

Thr Asn Ile Leu Met Leu Asp Ser Ala Ser Leu Ala Gly Leu His Ala
 130                 135                 140

Leu Arg Phe Leu Phe Met Asp Gly Asn Cys Tyr Tyr Lys Asn Pro Cys
145                 150                 155                 160

Arg Gln Ala Leu Glu Val Ala Pro Gly Ala Leu Leu Gly Leu Gly Asn
             165                 170                 175

Leu Thr His Leu Ser Leu Lys Tyr Asn Asn Leu Thr Val Val Pro Arg
             180                 185                 190

Asn Leu Pro Ser Ser Leu Glu Tyr Leu Leu Leu Ser Tyr Asn Arg Ile
             195                 200                 205

Val Lys Leu Ala Pro Glu Asp Leu Ala Asn Leu Thr Ala Leu Arg Val
210                 215                 220

Leu Asp Val Gly Gly Asn Cys Arg Arg Cys Asp His Ala Pro Asn Pro
225                 230                 235                 240

Cys Met Glu Cys Pro Arg His Phe Pro Gln Leu His Pro Asp Thr Phe
                 245                 250                 255

Ser His Leu Ser Arg Leu Glu Gly Leu Val Leu Lys Asp Ser Ser Leu
             260                 265                 270

Ser Trp Leu Asn Ala Ser Trp Phe Arg Gly Leu Gly Asn Leu Arg Val
             275                 280                 285

Leu Asp Leu Ser Glu Asn Phe Leu Tyr Lys Cys Ile Thr Lys Thr Lys
290                 295                 300

Ala Phe Gln Gly Leu Thr Gln Leu Arg Lys Leu Asn Leu Ser Phe Asn
305                 310                 315                 320

Tyr Gln Lys Arg Val Ser Phe Ala His Leu Ser Leu Ala Pro Ser Phe
             325                 330                 335

Gly Ser Leu Val Ala Leu Lys Glu Leu Asp Met His Gly Ile Phe Phe
             340                 345                 350

Arg Ser Leu Asp Glu Thr Thr Leu Arg Pro Leu Ala Arg Leu Pro Met
             355                 360                 365

Leu Gln Thr Leu Arg Leu Gln Met Asn Phe Ile Asn Gln Ala Gln Leu
             370                 375                 380

Gly Ile Phe Arg Ala Phe Pro Gly Leu Arg Tyr Val Asp Leu Ser Asp
385                 390                 395                 400

Asn Arg Ile Ser Gly Ala Ser Glu Leu Thr Ala Thr Met Gly Glu Ala
                 405                 410                 415

Asp Gly Gly Glu Lys Val Trp Leu Gln Pro Gly Asp Leu Ala Pro Ala
             420                 425                 430

Pro Val Asp Thr Pro Ser Ser Glu Asp Phe Arg Pro Asn Cys Ser Thr
             435                 440                 445

Leu Asn Phe Thr Leu Asp Leu Ser Arg Asn Asn Leu Val Thr Val Gln
450                 455                 460
```

```
Pro Glu Met Phe Ala Gln Leu Ser His Leu Gln Cys Leu Arg Leu Ser
465                 470                 475                 480

His Asn Cys Ile Ser Gln Ala Val Asn Gly Ser Gln Phe Leu Pro Leu
            485                 490                 495

Thr Gly Leu Gln Val Leu Asp Leu Ser His Asn Lys Leu Asp Leu Tyr
        500                 505                 510

His Glu His Ser Phe Thr Glu Leu Pro Arg Leu Glu Ala Leu Asp Leu
    515                 520                 525

Ser Tyr Asn Ser Gln Pro Phe Gly Met Gln Gly Val Gly His Asn Phe
530                 535                 540

Ser Phe Val Ala His Leu Arg Thr Leu Arg His Leu Ser Leu Ala His
545                 550                 555                 560

Asn Asn Ile His Ser Gln Val Ser Gln Gln Leu Cys Ser Thr Ser Leu
            565                 570                 575

Arg Ala Leu Asp Phe Ser Gly Asn Ala Leu Gly His Met Trp Ala Glu
        580                 585                 590

Gly Asp Leu Tyr Leu His Phe Phe Gln Gly Leu Ser Gly Leu Ile Trp
        595                 600                 605

Leu Asp Leu Ser Gln Asn Arg Leu His Thr Leu Leu Pro Gln Thr Leu
610                 615                 620

Arg Asn Leu Pro Lys Ser Leu Gln Val Leu Arg Leu Arg Asp Asn Tyr
625                 630                 635                 640

Leu Ala Phe Phe Lys Trp Trp Ser Leu His Phe Leu Pro Lys Leu Glu
            645                 650                 655

Val Leu Asp Leu Ala Gly Asn Gln Leu Lys Ala Leu Thr Asn Gly Ser
        660                 665                 670

Leu Pro Ala Gly Thr Arg Leu Arg Arg Leu Asp Val Ser Cys Asn Ser
        675                 680                 685

Ile Ser Phe Val Ala Pro Gly Phe Phe Ser Lys Ala Lys Glu Leu Arg
690                 695                 700

Glu Leu Asn Leu Ser Ala Asn Ala Leu Lys Thr Val Asp His Ser Trp
705                 710                 715                 720

Phe Gly Pro Leu Ala Ser Ala Leu Gln Ile Leu Asp Val Ser Ala Asn
            725                 730                 735

Pro Leu His Cys Ala Cys Gly Ala Ala Phe Met Asp Phe Leu Leu Glu
        740                 745                 750

Val Gln Ala Ala Val Pro Gly Leu Pro Ser Arg Val Lys Cys Gly Ser
        755                 760                 765

Pro Gly Gln Leu Gln Gly Leu Ser Ile Phe Ala Gln Asp Leu Arg Leu
        770                 775                 780

Cys Leu Asp Glu Ala Leu Ser Trp Asp Cys
785                 790

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

Gly Gly Gly Gly Ser
1               5

<210> SEQ ID NO 3
<211> LENGTH: 208
```

```
<212> TYPE: PRT
<213> ORGANISM: Artificial Sequence
<220> FEATURE:
<223> OTHER INFORMATION: Synthetic Construct

<400> SEQUENCE: 3

Val Phe Leu Phe Pro Pro Lys Pro Lys Asp Thr Leu Met Ile Ser Arg
1               5                   10                  15

Thr Pro Glu Val Thr Cys Val Val Asp Val Ser His Glu Asp Pro
            20                  25                  30

Glu Val Lys Phe Asn Trp Tyr Val Asp Gly Val Glu Val His Asn Ala
        35                  40                  45

Lys Thr Lys Pro Arg Glu Glu Gln Tyr Asn Ser Thr Tyr Arg Val Val
    50                  55                  60

Ser Val Leu Thr Val Leu His Gln Asp Trp Leu Asn Gly Lys Glu Tyr
65                  70                  75                  80

Lys Cys Lys Val Ser Asn Lys Ala Leu Pro Ala Pro Ile Glu Lys Thr
                85                  90                  95

Ile Ser Lys Ala Lys Gly Gln Pro Arg Glu Pro Gln Val Tyr Thr Leu
            100                 105                 110

Pro Pro Ser Arg Asp Glu Leu Thr Lys Asn Gln Val Ser Leu Thr Cys
        115                 120                 125

Leu Val Lys Gly Phe Tyr Pro Ser Asp Ile Ala Val Glu Trp Glu Ser
    130                 135                 140

Asn Gly Gln Pro Glu Asn Asn Tyr Lys Thr Thr Pro Pro Val Leu Asp
145                 150                 155                 160

Ser Asp Gly Ser Phe Phe Leu Tyr Ser Lys Leu Thr Val Asp Lys Ser
                165                 170                 175

Arg Trp Gln Gln Gly Asn Val Phe Ser Cys Ser Val Met His Glu Ala
            180                 185                 190

Leu His Asn His Tyr Thr Gln Lys Ser Leu Ser Leu Ser Pro Gly Lys
        195                 200                 205

<210> SEQ ID NO 4
<211> LENGTH: 207
<212> TYPE: PRT
<213> ORGANISM: Artificial Sequence
<220> FEATURE:
<223> OTHER INFORMATION: Synthetic Construct

<400> SEQUENCE: 4

Val Phe Leu Phe Pro Pro Lys Pro Lys Asp Thr Leu Met Ile Ser Arg
1               5                   10                  15

Thr Pro Glu Val Thr Cys Val Val Asp Val Ser His Glu Asp Pro
            20                  25                  30

Glu Val Gln Phe Asn Trp Tyr Val Asp Gly Val Glu Val His Asn Ala
        35                  40                  45

Lys Thr Lys Pro Arg Glu Glu Gln Phe Asn Ser Thr Phe Arg Val Val
    50                  55                  60

Ser Val Leu Thr Val Val His Gln Asp Trp Leu Asn Gly Lys Glu Tyr
65                  70                  75                  80

Lys Cys Lys Val Ser Asn Lys Gly Leu Pro Ala Pro Ile Glu Lys Thr
                85                  90                  95

Ile Ser Lys Thr Lys Gly Gln Pro Arg Glu Pro Gln Val Tyr Thr Leu
            100                 105                 110

Pro Pro Ser Arg Glu Glu Met Thr Lys Asn Gln Val Ser Leu Thr Cys
        115                 120                 125
```

```
Leu Val Lys Gly Phe Tyr Pro Ser Asp Ile Ala Val Glu Trp Glu Ser
    130                 135                 140

Asn Gly Gln Pro Glu Asn Asn Tyr Lys Thr Thr Pro Pro Met Leu Asp
145                 150                 155                 160

Ser Asp Gly Ser Phe Phe Leu Tyr Ser Lys Leu Thr Val Asp Lys Ser
                165                 170                 175

Arg Trp Gln Gln Gly Asn Val Phe Cys Ser Val Met His Glu Ala Leu
            180                 185                 190

His Asn His Tyr Thr Gln Lys Ser Leu Ser Leu Ser Pro Gly Lys
        195                 200                 205

<210> SEQ ID NO 5
<211> LENGTH: 217
<212> TYPE: PRT
<213> ORGANISM: Artificial Sequence
<220> FEATURE:
<223> OTHER INFORMATION: Synthetic Construct

<400> SEQUENCE: 5

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Gly Leu Pro Ser Ser Ile Glu Lys Thr Ile Ser Lys Ala Lys Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215

<210> SEQ ID NO 6
<211> LENGTH: 5
<212> TYPE: PRT
<213> ORGANISM: Artificial Sequence
<220> FEATURE:
<223> OTHER INFORMATION: Synthetic Construct

<400> SEQUENCE: 6

Cys Pro Ser Cys Pro
```

<210> SEQ ID NO 7
<211> LENGTH: 1020
<212> TYPE: PRT
<213> ORGANISM: Artificial Sequence
<220> FEATURE:
<223> OTHER INFORMATION: Synthetic Construct

<400> SEQUENCE: 7

```
Met Leu Gly Thr Leu Pro Ala Phe Leu Pro Cys Glu Leu Gln Pro His
1               5                   10                  15

Gly Leu Val Asn Cys Asn Trp Leu Phe Leu Lys Ser Val Pro His Phe
            20                  25                  30

Ser Met Ala Ala Pro Arg Gly Asn Val Thr Ser Leu Ser Leu Ser Ser
        35                  40                  45

Asn Arg Ile His His Leu His Asp Ser Asp Phe Ala His Leu Pro Ser
    50                  55                  60

Leu Arg His Leu Asn Leu Lys Trp Asn Cys Pro Pro Val Gly Leu Ser
65                  70                  75                  80

Pro Met His Phe Pro Cys His Met Thr Ile Glu Pro Ser Thr Phe Leu
                85                  90                  95

Ala Val Pro Thr Leu Glu Glu Leu Asn Leu Ser Tyr Asn Asn Ile Met
            100                 105                 110

Thr Val Pro Ala Leu Pro Lys Ser Leu Ile Ser Leu Ser Leu Ser His
        115                 120                 125

Thr Asn Ile Leu Met Leu Asp Ser Ala Ser Leu Ala Gly Leu His Ala
    130                 135                 140

Leu Arg Phe Leu Phe Met Asp Gly Asn Cys Tyr Tyr Lys Asn Pro Cys
145                 150                 155                 160

Arg Gln Ala Leu Glu Val Ala Pro Gly Ala Leu Leu Gly Leu Gly Asn
                165                 170                 175

Leu Thr His Leu Ser Leu Lys Tyr Asn Asn Leu Thr Val Val Pro Arg
            180                 185                 190

Asn Leu Pro Ser Ser Leu Glu Tyr Leu Leu Leu Ser Tyr Asn Arg Ile
        195                 200                 205

Val Lys Leu Ala Pro Glu Asp Leu Ala Asn Leu Thr Ala Leu Arg Val
    210                 215                 220

Leu Asp Val Gly Gly Asn Cys Arg Arg Cys Asp His Ala Pro Asn Pro
225                 230                 235                 240

Cys Met Glu Cys Pro Arg His Phe Pro Gln Leu His Pro Asp Thr Phe
                245                 250                 255

Ser His Leu Ser Arg Leu Glu Gly Leu Val Leu Lys Asp Ser Ser Leu
            260                 265                 270

Ser Trp Leu Asn Ala Ser Trp Phe Arg Gly Leu Gly Asn Leu Arg Val
        275                 280                 285

Leu Asp Leu Ser Glu Asn Phe Leu Tyr Lys Cys Ile Thr Lys Thr Lys
    290                 295                 300

Ala Phe Gln Gly Leu Thr Gln Leu Arg Lys Leu Asn Leu Ser Phe Asn
305                 310                 315                 320

Tyr Gln Lys Arg Val Ser Phe Ala His Leu Ser Leu Ala Pro Ser Phe
                325                 330                 335

Gly Ser Leu Val Ala Leu Lys Glu Leu Asp Met His Gly Ile Phe Phe
            340                 345                 350

Arg Ser Leu Asp Glu Thr Thr Leu Arg Pro Leu Ala Arg Leu Pro Met
```

```
                355                 360                 365
Leu Gln Thr Leu Arg Leu Gln Met Asn Phe Ile Asn Gln Ala Gln Leu
    370                 375                 380
Gly Ile Phe Arg Ala Phe Pro Gly Leu Arg Tyr Val Asp Leu Ser Asp
385                 390                 395                 400
Asn Arg Ile Ser Gly Ala Ser Glu Leu Thr Ala Thr Met Gly Glu Ala
                405                 410                 415
Asp Gly Gly Glu Lys Val Trp Leu Gln Pro Gly Asp Leu Ala Pro Ala
            420                 425                 430
Pro Val Asp Thr Pro Ser Ser Glu Asp Phe Arg Pro Asn Cys Ser Thr
            435                 440                 445
Leu Asn Phe Thr Leu Asp Leu Ser Arg Asn Asn Leu Val Thr Val Gln
    450                 455                 460
Pro Glu Met Phe Ala Gln Leu Ser His Leu Gln Cys Leu Arg Leu Ser
465                 470                 475                 480
His Asn Cys Ile Ser Gln Ala Val Asn Gly Ser Gln Phe Leu Pro Leu
                485                 490                 495
Thr Gly Leu Gln Val Leu Asp Leu Ser His Asn Lys Leu Asp Leu Tyr
            500                 505                 510
His Glu His Ser Phe Thr Glu Leu Pro Arg Leu Glu Ala Leu Asp Leu
            515                 520                 525
Ser Tyr Asn Ser Gln Pro Phe Gly Met Gln Gly Val Gly His Asn Phe
    530                 535                 540
Ser Phe Val Ala His Leu Arg Thr Leu Arg His Leu Ser Leu Ala His
545                 550                 555                 560
Asn Asn Ile His Ser Gln Val Ser Gln Gln Leu Cys Ser Thr Ser Leu
                565                 570                 575
Arg Ala Leu Asp Phe Ser Gly Asn Ala Leu Gly His Met Trp Ala Glu
            580                 585                 590
Gly Asp Leu Tyr Leu His Phe Phe Gln Gly Leu Ser Gly Leu Ile Trp
            595                 600                 605
Leu Asp Leu Ser Gln Asn Arg Leu His Thr Leu Leu Pro Gln Thr Leu
    610                 615                 620
Arg Asn Leu Pro Lys Ser Leu Gln Val Leu Arg Leu Arg Asp Asn Tyr
625                 630                 635                 640
Leu Ala Phe Phe Lys Trp Trp Ser Leu His Phe Leu Pro Lys Leu Glu
                645                 650                 655
Val Leu Asp Leu Ala Gly Asn Gln Leu Lys Ala Leu Thr Asn Gly Ser
            660                 665                 670
Leu Pro Ala Gly Thr Arg Leu Arg Arg Leu Asp Val Ser Cys Asn Ser
            675                 680                 685
Ile Ser Phe Val Ala Pro Gly Phe Phe Ser Lys Ala Lys Glu Leu Arg
    690                 695                 700
Glu Leu Asn Leu Ser Ala Asn Ala Leu Lys Thr Val Asp His Ser Trp
705                 710                 715                 720
Phe Gly Pro Leu Ala Ser Ala Leu Gln Ile Leu Asp Val Ser Ala Asn
                725                 730                 735
Pro Leu His Cys Ala Cys Gly Ala Ala Phe Met Asp Phe Leu Leu Glu
            740                 745                 750
Val Gln Ala Ala Val Pro Gly Leu Pro Ser Arg Val Lys Cys Gly Ser
        755                 760                 765
Pro Gly Gln Leu Gln Gly Leu Ser Ile Phe Ala Gln Asp Leu Arg Leu
    770                 775                 780
```

-continued

```
Cys Leu Asp Glu Ala Leu Ser Trp Asp Cys Arg Ser Pro Pro Cys Pro
785                 790                 795                 800
Ser Cys Pro Ala Pro Glu Phe Leu Gly Gly Pro Ser Val Phe Leu Phe
                805                 810                 815
Pro Pro Lys Pro Lys Asp Thr Leu Met Ile Ser Arg Thr Pro Glu Val
            820                 825                 830
Thr Cys Val Val Val Asp Val Ser Gln Glu Asp Pro Glu Val Gln Phe
        835                 840                 845
Asn Trp Tyr Val Asp Gly Val Glu Val His Asn Ala Lys Thr Lys Pro
    850                 855                 860
Arg Glu Glu Gln Phe Asn Ser Thr Tyr Arg Val Val Ser Val Leu Thr
865                 870                 875                 880
Val Leu His Gln Asp Trp Leu Asn Gly Lys Glu Tyr Lys Cys Lys Val
            885                 890                 895
Ser Asn Lys Gly Leu Pro Ser Ser Ile Glu Lys Thr Ile Ser Lys Ala
            900                 905                 910
Lys Gly Gln Pro Arg Glu Pro Gln Val Tyr Thr Leu Pro Pro Ser Gln
        915                 920                 925
Glu Glu Met Thr Lys Asn Gln Val Ser Leu Thr Cys Leu Val Lys Gly
    930                 935                 940
Phe Tyr Pro Ser Asp Ile Ala Val Glu Trp Glu Ser Asn Gly Gln Pro
945                 950                 955                 960
Glu Asn Asn Tyr Lys Thr Thr Pro Pro Val Leu Asp Ser Asp Gly Ser
                965                 970                 975
Phe Phe Leu Tyr Ser Arg Leu Thr Val Asp Lys Ser Arg Trp Gln Glu
            980                 985                 990
Gly Asn Val Phe Ser Cys Ser Val Met His Glu Ala Leu His Asn His
        995                 1000                1005
Tyr Thr Gln Lys Ser Leu Ser Leu Ser Pro Gly Lys
    1010                1015                1020
```

TLR9 LIGAND TRAP

CROSS-REFERENCE TO RELATED APPLICATIONS

This application is a Continuation of International Application No. PCT/US2019/047706, filed Aug. 22, 2019, which claims benefit of U.S. Provisional Application No. 62/721,832, filed Aug. 23, 2018, which is hereby incorporated herein by reference in its entirety.

SEQUENCE LISTING

This application contains a sequence listing filed in electronic form as an ASCII.txt file entitled "320803-2270 Sequence Listing_ST25" created on Aug. 19, 2019. The content of the sequence listing is incorporated herein in its entirety.

BACKGROUND

Attempts to develop selective therapeutics targeting malignant stem cells in myelodysplastic syndrome (MDS) has historically been limited by the absence of disease-specific surface markers that distinguish the malignant clone from normal hematopoietic stem and progenitor cells (HSPC).

SUMMARY

MDS HSPC translocate endosomal Toll-Like receptor (TLR)-9 to the plasma membrane, thereby sensitizing these clonal propagating cells to respective ligands in the microenvironment. TLR9 is the cognate receptor for RNA:DNA hybrids (R-loops) and unmethylated CpG oligonucleotides in oxidized mitochondrial DNA, the latter of which is abundant in the bone marrow microenvironment as a result of massive medullary pyroptotic cytolytic cell death. Both ligands are important danger-associated molecular patterns (DAMPs) triggering innate immune activation and chronic inflammation that contributes to MDS pathogenesis.

In an effort to neutralize these DAMPs and disrupt this feed-forward inflammatory cascade, a chimeric protein was designed fusing the external epitopes of TLR9 to the Fc domain of human IgG4 to serve as a decoy receptor or ligand trap recognizing extracellular RNA:DNA hybrids (R-loops) and oxidized mitochondrial DNA. Neutralization of these important ligands that stimulate MDS HSPC is intended to suppress pyroptosis and the liberation of inflammatory cytokines directing ineffective hematopoiesis. This TLR9-IgG4 chimera binds to its cognate TLR9 ligands (e.g., CpG) in a concentration-dependent fashion and augments colony forming capacity (CFC) in primary MDS bone marrow specimens when compared with IgG4 isotype control.

Disclosed herein are chimeric ligand trap proteins that comprise a soluble TLR9 receptor polypeptide and at least one heterologous protein, wherein the TLR9 Ligand Trap is capable of binding TLR9 ligands, such as CpG. In various embodiments, the heterologous protein is an Fc domain. In various embodiments, the Fc domain is a human IgG Fc domain. In some embodiments, the Fc domain is derived from a human IgG1 heavy chain constant domain sequence. In some embodiments, the Fc domain is derived from a human IgG2 heavy chain constant domain sequence. In some embodiments, the Fc domain is derived from a human IgG4 heavy chain constant domain sequence.

In some embodiments, the molecule is defined by the formula:

TLR9-Fc, wherein "TLR9" represents the TLR9 extracellular domain peptide, wherein "Fc" represents an IgG Fc domain, and wherein "-" represents an optional linker and/or hinge domain.

In another aspect, the present disclosure provides isolated nucleic acid molecules encoding the disclosed TLR9 Ligand Trap polypeptides. In another aspect, the present disclosure provides vectors comprising the nucleic acids described herein. In various embodiments, the vector is an expression vector. In another aspect, the present disclosure provides isolated cells comprising the nucleic acids of the disclosure. In various embodiments, the cell is a host cell comprising the expression vector of the disclosure. In another aspect, methods of making the TLR9 Ligand Trap proteins are provided by culturing the host cells under conditions promoting expression of the proteins or polypeptides.

In another aspect, the present disclosure provides a pharmaceutical composition comprising the isolated TLR9 Ligand Trap polypeptides in admixture with a pharmaceutically acceptable carrier.

In another aspect, the present disclosure provides a method of treating a TLR9-expressing cancer in a subject that involves administering to the subject a therapeutically effective amount of a disclosed pharmaceutical composition. In some cases, the cancer comprises a myelodysplastic syndrome (MDS). For example, the cancer can be non-del (5q) MDS. For example, cancers of the skin, esophagous, colon, rectum, liver, lung, and uterus have been shown to have increased TLR9 protein expression. In some cases, the method further involves assaying a biopsy sample from the subject for TLR9 expression prior to treatment.

Cell death in MDS arises from pyroptosis mediated through the Nod-like receptor 3 (NLRP3) inflammasome. Oxidized DNA (oxDNA) serves as a danger-associated molecular pattern (DAMP) that can amplify cell death by direct engagement and activation of NLRP3, as well as the DNA-recognition receptors Toll-like receptor (TLR)-9 and cGAS-STI NG. Upon inflammasome activation, caspase-1 is bridged to the nod like receptor NLRP3 through the adapter molecule, ASC, then undergoes autocleavage which subsequently cleaves pro-IL1β to drive a feed forward inflammatory cascade. Oxidized mitochondrial DNA (ox-mtDNA) leaks to the cytosol upon mitochondrial membrane depolarization and is consequently released from pyroptotic progenitors upon cytolysis. Therefore, in some embodiments, ox-mtDNA is elevated in the peripheral blood (PB) of MDS patients and correlates with surrogate markers of pyroptosis. As disclosed herein, ox-mtDNA is profoundly elevated in the peripheral blood of MDS patients compared to healthy donors, and increases directly with surrogate biomarkers of pyroptosis.

In some embodiments, the disclosed TLR9 Ligand Trap is used to treat a subject with MDS. In some embodiments, the disclosed methods involve assaying a sample (such as peripheral blood) from the subject for a surrogate marker of pyroptosis, such as ox-mtDNA, apoptosis associated speck-like protein containing a CARD (ASC), or any combination thereof. In these embodiments, the disclosed method can involve treating the subject with the disclosed TLR9 Ligand Trap if the subject is positive for pyroptosis. In some embodiments, the subject has been diagnosed with lower-risk or intermediate-1 MDS where the priority is amelioration of symptoms by the treatment of cytopenias to improve quality of life.

In some embodiments, plasma ox-mtDNA is a disease activity biomarker for autoimmune diseases, such as psoriatic arthritis, systemic lupus erythematosus (SLE), and rheumatoid arthritis (RA). Therefore, in another aspect, the present disclosure provides a method of treating autoimmune diseases, such as psoriatic arthritis, systemic lupus erythematosus (SLE), or rheumatoid arthritis (RA), in a subject that involves administering to the subject a therapeutically effective amount of a disclosed pharmaceutical composition. In some embodiments, the disclosed methods involve assaying a sample (such as peripheral blood) from the subject for a surrogate marker of pyroptosis, such as ox-mtDNA, apoptosis associated speck-like protein containing a CARD (ASC), or any combination thereof. In these embodiments, the disclosed method can involve treating the subject with the disclosed TLR9 Ligand Trap if the subject is positive for pyroptosis.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4A is an image showing oxDNA, TLR9, and DAPI staining in wildtype and Tet2$^{-/-}$ murine HSPCs. FIGS. 4B and 4C contain bar graphs showing elevated OxDNA in supernatants of epigenetic EZH2$^{-/-}$ (FIG. 4B) and Tet2$^{-/-}$ (FIG. 4C) mutants. FIG. 4D is a graph showing ox-mtDNA in wildtype and Tet2$^{-/-}$ murine HSPCs. FIG. 4E is a bar graph showing MFI of wildtype and Tet2$^{-/-}$ murine HSPCs.

FIGS. 12A and 12B show OxDNA levels are significantly higher in LR patients compared to HR patients (FIG. 12A) and all other hematologic malignancies (p≤0.03) except CLL which has been previously shown to have increased oxDNA in relation to unfavorable cytogenetics (FIG. 12B). FIG. 12C shows OxDNA demonstrates a AUC/ROC of 0.964 with a specificity of 0.777 and sensitivity of 0.95 demonstrating the utility of oxDNA as a strong biomarker for MDS. FIG. 12D shows OxDNA is slightly increased in LR patient bone marrow compared to peripheral blood. FIG. 12E shows OxDNA is significantly released as a result of NLRP3 inflammasome activation.

FIG. 13A shows OxDNA positively correlates with established inflammasome biomarkers and DAMP-activators; ASC specks, S100A9, and S100A8 p<0.0001 (Pearson). FIG. 13B shows MDS patients demonstrate significantly higher CXCL10 and ISG15 levels by gene expression array in MDS patients compared to normal donors suggesting increased activation of DNA sensing pathways. FIG. 13C shows Ox-mtDNA treatment of U937 cells results in inflammasome activation, demonstrated by western blot and caspase-1 cleavage. FIG. 13D shows endogenous TLR9 levels in THP-1 (Low), U937 (Med), and SKM-1 (High). FIG. 13E shows SKM-1 and U937 cells are sensitive to ox-mtDNA in a dose, time, and TLR9 expression dependent manner.

FIG. 14C shows IP NLRP3 probed for mitochondrial genes by PCR. FIG. 14D shows intracellular ox-mtDNA co-localizes with NLRP3 in in driving mutation MDS Murine Models. FIG. 14E shows SKM-1 and U937 cells were cultured for >20 passages in EtBr to deplete mtDNA, these cells will be crucial for future investigations.

FIG. 15A shows TLR9 surface expression is increased in MDS patient mononuclear cells and in particular CD34+ hematopoietic stem cells. FIG. 15B shows OxDNA is significantly increased in a murine model of MDS: Tet2-/- C57BL/6 compared to the wildtype control as shown by flow cytometry (p=0.05). FIG. 15C shows confocal IF imaging demonstrates strong co-localization of TLR9 (Alexa 647) and oxDNA (FITC) in the TET2-/- MDS model. In MDS patient BM-MNC there is increased oxDNA that is strongly co-localized with TLR9 (FIG. 15D) and similarly seen co-localization with cGAS (FIG. 15E) which is not observed in normal BM-MNCs. These results suggest that cGAS and TLR9 pathways may be a mechanism by which oxDNA is recognized to activate the inflammasome. 630×. FIG. 15F shows CRISPR knockout of TLR9 in SKM-1 and U937. FIG. 15G shows TLR9 depleted clones are do not exhibit the same increase cleaved caspase-1 and mature IL-1β in response to oxmtDNA treatment as seen in their scrambled control.

FIG. 16 is an illustration showing MDS hematopoietic stem cells (HSC) inflammasome activation being driven by oxidized mitochondrial DNA through the cGAS-Sting and/or TLR9 pathways. This is followed by pyroptosis and release of ASC specs and oxDNA into the plasma resulting in a feedforward mechanism of inflammasome activation in neighboring HSCs.

DETAILED DESCRIPTION

Figure 1:
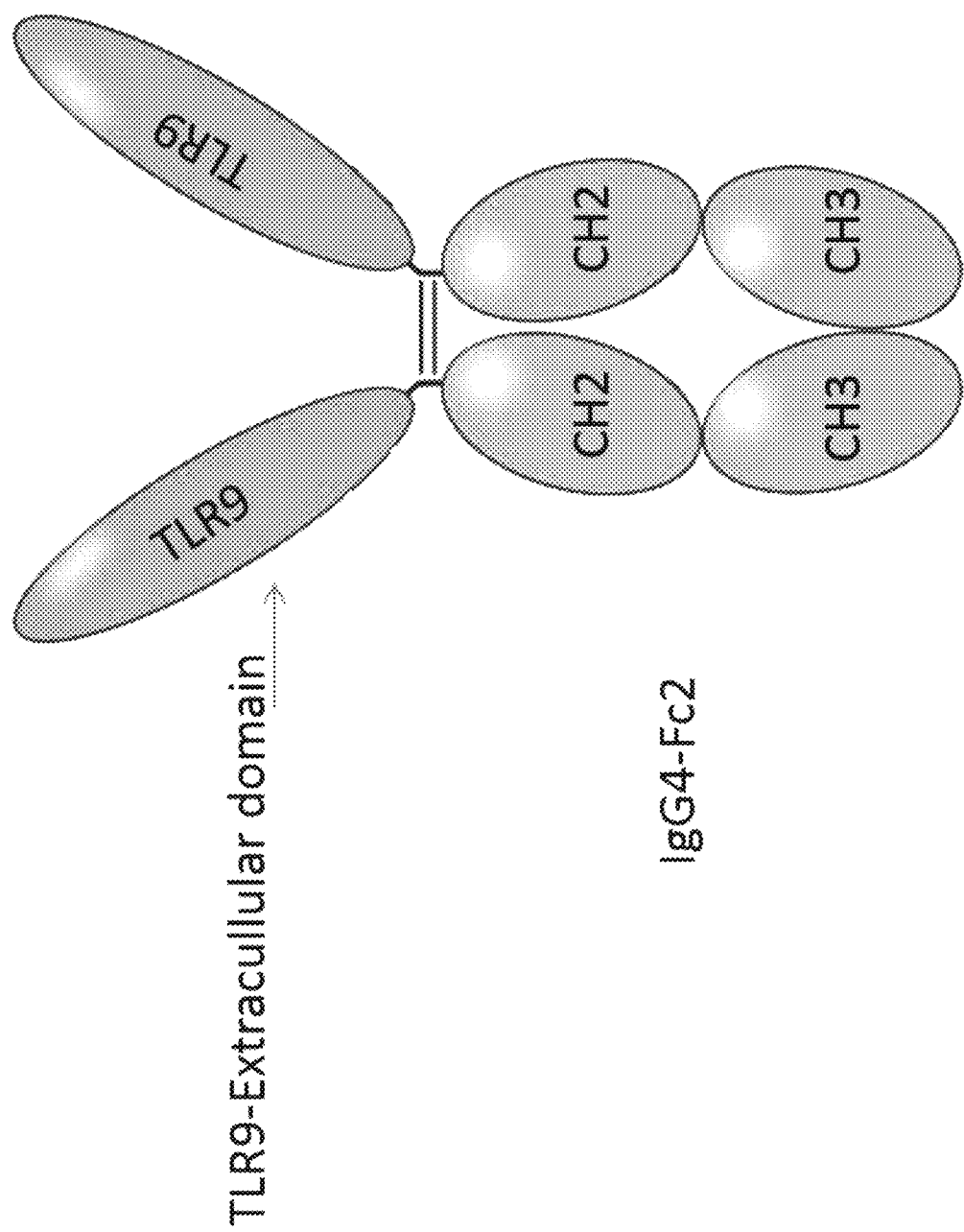
FIG. 1 is a schematic of an embodiment of the disclosed TLR9-IgG4 chimera ligand trap.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

Definitions

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "Fc region" as used herein defines the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a CH2 domain and a CH3 domain, and optionally comprises a CH4 domain. The Fc portion of an antibody mediates several important effector functions e.g. cytokine induction, ADCC, phagocytosis, complement dependent cytotoxicity (CDC) and half-life/clearance rate of antibody and antigen-antibody complexes (e.g., the neonatal FcR (FcRn) binds to the Fc region of IgG at acidic pH in the endosome and protects IgG from degradation, thereby contributing to the long serum half-life of IgG). Replacements of amino acid residues in the Fc portion to alter antibody effector function are known in the art (see, e.g., Winter et al., U.S. Pat. Nos. 5,648,260 and 5,624,821).

A "fusion protein" or "fusion polypeptide" refers to a hybrid polypeptide which comprises polypeptide portions from at least two different polypeptides. The portions may be from proteins of the same organism, in which case the fusion protein is said to be "intraspecies", "intragenic", etc. In various embodiments, the fusion polypeptide may comprise one or more amino acid sequences linked to a first polypeptide. In the case where more than one amino acid sequence is fused to a first polypeptide, the fusion sequences may be multiple copies of the same sequence, or alternatively, may be different amino acid sequences. A first polypeptide may be fused to the N-terminus, the C-terminus, or the N- and C-terminus of a second polypeptide. Furthermore, a first polypeptide may be inserted within the sequence of a second polypeptide.

The term "linker" is art-recognized and refers to a molecule or group of molecules connecting two compounds, such as two polypeptides. The linker may be comprised of a single linking molecule or may comprise a linking molecule and a spacer molecule, intended to separate the linking molecule and a compound by a specific distance.

The term "nucleic acid" refers to a polymeric form of nucleotides, either ribonucleotides or deoxynucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "polypeptide fragment" as used herein refers to a polypeptide that has an amino-terminal and/or carboxy-terminal deletion as compared to a corresponding full-length protein. A fragment can further comprise, at either or both of its ends, one or more additional amino acids, for example, a sequence of amino acids from a different naturally-occurring protein (e.g., an Fc domain) or an artificial amino acid sequence (e.g., an artificial linker sequence).

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

TLR9 Ligand Trap

Disclosed herein are chimeric ligand trap proteins that comprise a soluble TLR9 polypeptide and at least one heterologous protein, wherein the TLR9 Ligand Trap is capable of binding TLR9 ligands, such as CpG.

TLR9 Polypeptide

The TLR9 polypeptide of the disclosed TLR9 Ligand Trap is a polypeptide comprising at least a portion of the TLR9 extracellular domain capable of binding TLR9 ligands, such as CpG.

In some embodiments, TLR9 extracellular domain can have the amino acid sequence:

(SEQ ID NO: 1)
MLGTLPAFLPCELQPHGLVNCNWLFLKSVPHFSMAAPRGNVTSLSLSSN

RIHHLHDSDFAHLPSLRHLNLKWNCPPVGLSPMHFPCHMTIEPSTFLAV

PTLEELNLSYNNIMTVPALPKSLISLSLSHTNILMLDSASLAGLHALRF

-continued
LFMDGNCYYKNPCRQALEVAPGALLGLGNLTHLSLKYNNLTVVPRNLPS

SLEYLLLSYNRIVKLAPEDLANLTALRVLDVGGNCRRCDHAPNPCMECP

RHFPQLHPDTFSHLSRLEGLVLKDSSLSWLNASWFRGLGNLRVLDLSEN

FLYKCITKTKAFQGLTQLRKLNLSFNYQKRVSFAHLSLAPSFGSLVALK

ELDMHGIFFRSLDETTLRPLARLPMLQTLRLQMNFINQAQLGIFRAFPG

LRYVDLSDNRISGASELTATMGEADGGEKVWLQPGDLAPAPVDTPSSED

FRPNCSTLNFTLDLSRNNLVTVQPEMFAQLSHLQCLRLSHNCISQAVNG

SQFLPLTGLQVLDLSHNKLDLYHEHSFTELPRLEALDLSYNSQPFGMQG

VGHNFSFVAHLRTLRHLSLAHNNIHSQVSQQLCSTSLRALDFSGNALGH

MWAEGDLYLHFFQGLSGLIWLDLSQNRLHTLLPQTLRNLPKSLQVLRLR

DNYLAFFKWWSLHFLPKLEVLDLAGNQLKALTNGSLPAGTRLRRLDVSC

NSISFVAPGFFSKAKELRELNLSANALKTVDHSWFGPLASALQILDVSA

NPLHCACGAAFMDFLLEVQAAVPGLPSRVKCGSPGQLQGLSIFAQDLRL

CLDEALSWDC, or a variant thereof having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:1, or a fragment of SEQ ID NO:1 or a variant of SEQ ID NO:1 having at least 100, 110, 120, 130, 140, 141, 142, 143, 144, 145, 156, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 420, 430, 440, 441, 442, 443, 444, 445, 456, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 600, 700, 750, 760, 780, 790, 791, 792, or 793 contiguous amino acids.

IgG Fc Domain

In some embodiments, the heterologous protein is an Fc domain. In some embodiments, the Fc domain is a human IgG Fc domain. In some embodiments, the Fc domain is derived from a human IgG1 heavy chain constant domain sequence. In some embodiments, the Fc domain is derived from a human IgG2 heavy chain constant domain sequence. In some embodiments, the Fc domain is derived from a human IgG4 heavy chain constant domain sequence.

For example, an IgG1 Fc domain can have the amino acid sequence:

```
                                          (SEQ ID NO: 3)
VFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTIS

KAKGQPREPQVYTLPPSRDELTKNQVSLTCLVKGFYPSDIAVEWESNGQ

PENNYKTTPPVLDSDGSFFLYSKLTVDKSRWQQGNVFSCSVMHEALHNH

YTQKSLSLSPGK,
``` or a variant thereof having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:3.

For example, an IgG2 Fc domain can have the amino acid sequence:

```
                                          (SEQ ID NO: 4)
VFLFPPKPKDTLMISRTPEVTCVVVDVSHEDPEVQFNWYVDGVEVHNAK

TKPREEQFNSTFRVVSVLTVVHQDWLNGKEYKCKVSNKGLPAPIEKTIS

KTKGQPREPQVYTLPPSREEMTKNQVSLTCLVKGFYPSDIAVEWESNGQ

PENNYKTTPPMLDSDGSFFLYSKLTVDKSRWQQGNVFSCSVMHEALHNHY

TQKSLSLSPGK,
``` or a variant thereof having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:4.

For example, an IgG4 Fc domain can have the amino acid sequence:

```
                                          (SEQ ID NO: 5)
APEFLGGPSVFLFPPKPKDTLMISRTPEVTCVVVDVSQEDPEVQFNWYV

DGVEVHNAKTKPREEQFNSTYRVVSVLTVLHQDWLNGKEYKCKVSNKGL

PSSIEKTISKAKGQPREPQVYTLPPSQEEMTKNQVSLTCLVKGFYPSDI

AVEWESNGQPENNYKTTPPVLDSDGSFFLYSRLTVDKSRWQEGNVFSCS

VMHEALHNHYTQKSLSLSLGK,
``` or a variant thereof having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:5

Linkers

The disclose TLR9 Ligand Traps can optionally further comprise a "linker" or "hinge linker" sequence. In various embodiments, the heterologous protein is attached to the TLR9 polypeptide by a linker or a hinge linker peptide. The linker and/or hinge linker may be an artificial sequence of between 5, 10, 15, 20, 30, 40 or more amino acids that are relatively free of secondary structure. In various embodiments, the linkers comprise amino acids selected from glycine, alanine, proline, asparagine, glutamine, and lysine. In various embodiments, a linker is made up of a majority of amino acids that are sterically unhindered, such as glycine and alanine, and are polyglycines (particularly (Gly)5, (Gly)8, poly(Gly-Ala), and polyalanines. In various embodiments, the linker is rich in G/S content (e.g., at least about 60%, 70%, 80%, 90%, or more of the amino acids in the linker are G or S. In various embodiments, the linker has a (GGGGS (SEQ ID NO: 2))n motif, wherein n=1-6. Such linkers and hinge linkers have been described extensively in art (see, e.g., U.S. Pat. No. 8,410,043, which is incorporated by reference herein for the purposes of teaching such linkers.

In some embodiments, the hinge linker comprises the amino acid sequence CPSCP (SEQ ID NO:6).

Linkers may also be non-peptide linkers. For example, alkyl linkers such as —NH—(CH2)n-C(O)—, wherein s=2-20 can be used. These alkyl linkers may further be substituted by any non-sterically hindering group such as lower alkyl (e.g., 01-06) lower acyl, halogen (e.g., CI, Br), CN, NH2, phenyl, etc.

Example Embodiment

Therefore, in some embodiments, the disclosed TLR9 Ligand Trap (TLR9 ectodomain—hinge region—IgG4Fc) comprises the amino acid sequence:

```
                                          (SEQ ID NO: 7)
MLGTLPAFLPCELQPHGLVNCNWLFLKSVPHFSMAAPRGNVTSLSLSSN

RIHHLHDSDFAHLPSLRHLNLKWNCPPVGLSPMHFPCHMTIEPSTFLAV

PTLEELNLSYNNIMTVPALPKSLISLSLSHTNILMLDSASLAGLHALRF

LFMDGNCYYKNPCRQALEVAPGALLGLGNLTHLSLKYNNLTVVPRNLPS

SLEYLLLSYNRIVKLAPEDLANLTALRVLDVGGNCRRCDHAPNPCMECP

RHFPQLHPDTFSHLSRLEGLVLKDSSLSWLNASWFRGLGNLRVLDLSEN

FLYKCITKTKAFQGLTQLRKLNLSFNYQKRVSFAHLSLAPSFGSLVALK

ELDMHGIFFRSLDETTLRPLARLPMLQTLRLQMNFINQAQLGIFRAFPG

LRYVDLSDNRISGASELTATMGEADGGEKVWLQPGDLAPAPVDTPSSED

FRPNCSTLNFTLDLSRNNLVTVQPEMFAQLSHLQCLRLSHNCISQAVNG

SQFLPLTGLQVLDLSHNKLDLYHEHSFTELPRLEALDLSYNSQPFGMQG

VGHNFSFVAHLRTLRHLSLAHNNIHSQVSQQLCSTSLRALDFSGNALGH

MWAEGDLYLHFFQGLSGLIWLDLSQNRLHTLLPQTLRNLPKSLQVLRLR

DNYLAFFKWWSLHFLPKLEVLDLAGNQLKALTNGSLPAGTRLRRLDVSC

NSISFVAPGFFSKAKELRELNLSANALKTVDHSWFGPLASALQILDVSA

NPLHCACGAAFMDFLLEVQAAVPGLPSRVKCGSPGQLQGLSIFAQDLRL

CLDEALSWDCRSPPCPSCPAPEFLGGPSVFLFPPKPKDTLMISRTPEVT

CVVVDVSQEDPEVQFNWYVDGVEVHNAKTKPREEQFNSTYRVVSVLTVL

HQDWLNGKEYKCKVSNKGLPSSIEKTISKAKGQPREPQVYTLPPSQEEM

TKNQVSLTCLVKGFYPSDIAVEWESNGQPENNYKTTPPVLDSDGSFFLY

SRLTVDKSRWQEGNVFSCSVMHEALHNHYTQKSLSLSPGK,
``` or a variant thereof having at least 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:7.

Molecular Configurations

It is understood that the different elements of the hybrid TLR9 Ligand Trap may be arranged in any manner that is consistent with the desired functionality. For example, a heterologous protein may be placed C-terminal to a TLR9 polypeptide, or alternatively the TLR9 polypeptide may be placed C-terminal to a heterologous domain. The TLR9 polypeptide domain and the heterologous domain need not be adjacent, and additional domains or amino acid sequences may be included C- or N-terminal to either domain or between the domains (i.e. include a linker described herein). An exemplary molecular configurations for the TLR9 Ligand Trap is depicted in FIG. 1

An exemplary configuration of a synthetic DNA cassette encoding a TLR9 Ligand Trap can be generally described as comprising the following elements: 1) a signal peptide (or leader sequence) placed at the N-terminus, which can be either the native signal peptide of TLR9 or any surrogate signal peptide capable of mediating the processing and secretion of secreted proteins; 2) a TLR9 polypeptide sequence (e.g., SEQ ID NO:1) fused to the signal peptide sequence; 3) a peptide linker/hinge sequence, and 4) an Fc domain fused to the TLR9 polypeptide sequence by the peptide/hinge linker.

Polynucleotides

In another aspect, the present disclosure provides isolated nucleic acid molecules comprising a polynucleotide encoding a TLR9 Ligand Trap polypeptide of the present disclosure. The subject nucleic acids may be single-stranded or double stranded. Such nucleic acids may be DNA or RNA molecules. DNA includes, for example, cDNA, genomic DNA, synthetic DNA, DNA amplified by PCR, and combinations thereof. Genomic DNA encoding polypeptides can be obtained from genomic libraries which are available for a number of species. Synthetic DNA is available from chemical synthesis of overlapping oligonucleotide fragments followed by assembly of the fragments to reconstitute part or all of the coding regions and flanking sequences. RNA may be obtained from prokaryotic expression vectors which direct high-level synthesis of mRNA, such as vectors using T7 promoters and RNA polymerase. cDNA is obtained from libraries prepared from mRNA isolated from various tissues. The DNA molecules of the disclosure include full-length genes as well as polynucleotides and fragments thereof. The full-length gene may also include sequences encoding the N-terminal signal sequence.

Such nucleic acids may be used, for example, in methods for making the TLR9 Ligand Trap polypeptides. In various embodiments, the nucleic acid sequences of the present disclosure can be isolated, recombinant, and/or fused with a heterologous nucleotide sequence, or in a DNA library.

In various embodiments, the present disclosure provides nucleic acid molecules which hybridize under stringent or moderate conditions with the polypeptide-encoding regions of the polynucleotides described herein. One of ordinary skill in the art will understand readily that appropriate stringency conditions, which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

In various embodiments, the recombinant nucleic acids of the present disclosure may be operably linked to one or more regulatory nucleotide sequences in an expression construct. Regulatory sequences are art-recognized and are selected to direct expression of the TLR9 Ligand Trap polypeptide. Accordingly, the term regulatory sequence includes promoters, enhancers, and other expression control elements. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the present disclosure. The promoters may be either naturally occurring promoters, or hybrid promoters that combine elements of more than one promoter. An expression construct may be present in a cell on an episome, such as a plasmid, or the expression construct may be inserted in a chromosome. In various embodiments, the expression vector contains a selectable marker gene to allow the selection of transformed host cells. Selectable marker genes are well known in the art and will vary with the host cell used.

In another aspect of the present disclosure, the subject nucleic acid is provided in an expression vector comprising a nucleotide sequence encoding a TLR9 Ligand Trap polypeptide and operably linked to at least one regulatory sequence. The term "expression vector" refers to a plasmid, phage, virus or vector for expressing a polypeptide from a polynucleotide sequence. Vectors suitable for expression in host cells are readily available and the nucleic acid molecules are inserted into the vectors using standard recombinant DNA techniques. Such vectors can include a wide variety of expression control sequences that control the expression of a DNA sequence when operatively linked to it may be used in these vectors to express DNA sequences encoding a TLR9 Ligand Trap polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., PhoS, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

This present disclosure also pertains to a host cell transfected with a recombinant gene including a nucleotide sequence coding an amino acid sequence for one or more of the subject TLR9 Ligand Trap polypeptides. The host cell may be any prokaryotic or eukaryotic cell. For example, a TLR9 Ligand Trap polypeptide of the present disclosure may be expressed in bacterial cells such as E. coli, insect cells (e.g., using a baculovirus expression system), yeast, or mammalian cells. Other suitable host cells are known to those skilled in the art.

Accordingly, the present disclosure further pertains to methods of producing the subject TLR9 Ligand Trap polypeptides. For example, a host cell transfected with an expression vector encoding a TLR9 Ligand Trap polypeptide can be cultured under appropriate conditions to allow expression of the TLR9 Ligand Trap polypeptide to occur. The TLR9 Ligand Trap polypeptide may be secreted and isolated from a mixture of cells and medium containing the TLR9 Ligand Trap polypeptide. Alternatively, the TLR9 Ligand Trap polypeptide may be retained cytoplasmically or in a membrane fraction and the cells harvested, lysed and the protein isolated. A cell culture includes host cells, media and other byproducts. Suitable media for cell culture are well known in the art.

The polypeptides and proteins of the present disclosure can be purified according to protein purification techniques are well known to those of skill in the art. These techniques involve, at one level, the crude fractionation of the proteinaceous and non-proteinaceous fractions. Having separated the peptide polypeptides from other proteins, the peptide or polypeptide of interest can be further purified using chromatographic and electrophoretic techniques to achieve partial or complete purification (or purification to homogeneity). The term "isolated polypeptide" or "purified polypeptide" as used herein, is intended to refer to a composition, isolatable from other components, wherein the polypeptide is purified to any degree relative to its naturally-obtainable state. A purified polypeptide therefore also refers to a polypeptide that is free from the environment in which it may naturally occur. Generally, "purified" will refer to a polypeptide composition that has been subjected to fractionation to remove various other components, and which composition substantially retains its expressed biological activity. Where the term "substantially purified" is used, this designation will refer to a peptide or polypeptide composition in which the polypeptide or peptide forms the major component of the composition, such as constituting about 50%, about 60%, about 70%, about 80%, about 85%, or about 90% or more of the proteins in the composition.

Various techniques suitable for use in purification will be well known to those of skill in the art. These include, for example, precipitation with ammonium sulphate, PEG, antibodies (immunoprecipitation) and the like or by heat denaturation, followed by centrifugation; chromatography such as affinity chromatography (Protein-A columns), ion exchange, gel filtration, reverse phase, hydroxylapatite, hydrophobic interaction chromatography; isoelectric focusing; gel electrophoresis; and combinations of these techniques. As is generally known in the art, it is believed that the order of conducting the various purification steps may be changed, or that certain steps may be omitted, and still result in a suitable method for the preparation of a substantially purified polypeptide.

Pharmaceutical Composition

Also disclosed is a pharmaceutical composition comprising a molecule disclosed herein in a pharmaceutically acceptable carrier. Pharmaceutical carriers are known to those skilled in the art. These most typically would be standard carriers for administration of drugs to humans, including solutions such as sterile water, saline, and buffered solutions at physiological pH. For example, suitable carriers and their formulations are described in Remington: The Science and Practice of Pharmacy (21 ed.) ed. P P. Gerbino, Lippincott Williams & Wilkins, Philadelphia, PA. 2005. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. The solution should be RNAse free. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Methods of Treatment

Also disclosed is a method for treating a TLR9-expressing cancer, such as a myelodysplastic syndrome (MDS), in a subject by administering to the subject a therapeutically effective amount of the disclosed pharmaceutical composition. The method can further involve administering to the subject lenalidomide, or an analogue or derivative thereof.

In some cases, the method further involves assaying a biopsy sample from the subject for TLR9 expression prior to treatment. This can be done using routine methods, such as immunodetection methods. Many types and formats of immunoassays are known and all are suitable for detecting the disclosed biomarkers. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

The disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

The compositions disclosed herein may be administered prophylactically to patients or subjects who are at risk for a TLR9-expressing cancer. Thus, the method can further comprise identifying a subject at risk for a TLR9-expressing cancer prior to administration of the herein disclosed compositions.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. A typical daily dosage of the disclosed composition used alone might range from about 1 μg/kg to up to 100 mg/kg of body weight or more per day, depending on the factors mentioned above.

In some embodiments, the molecule is administered in a dose equivalent to parenteral administration of about 0.1 ng to about 100 g per kg of body weight, about 10 ng to about 50 g per kg of body weight, about 100 ng to about 1 g per kg of body weight, from about 1 μg to about 100 mg per kg of body weight, from about 1 μg to about 50 mg per kg of body weight, from about 1 mg to about 500 mg per kg of body weight; and from about 1 mg to about 50 mg per kg of body weight. Alternatively, the amount of molecule administered to achieve a therapeutic effective dose is about 0.1 ng, 1 ng, 10 ng, 100 ng, 1 μg, 10 μg, 100 μg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

The disclosed TLR9 Ligand Trap can be used in combination with any compound, moiety or group which has a cytotoxic or cytostatic effect. Drug moieties include chemotherapeutic agents, which may function as microtubulin inhibitors, mitosis inhibitors, topoisomerase inhibitors, or DNA intercalators, and particularly those which are used for cancer therapy.

The disclosed TLR9 Ligand Trap can be used in combination with a checkpoint inhibitor. The two known inhibitory checkpoint pathways involve signaling through the cytotoxic T-lymphocyte antigen-4 (CTLA-4) and programmed-death 1 (PD-1) receptors. These proteins are members of the CD28-B7 family of cosignaling molecules that play important roles throughout all stages of T cell function. The PD-1 receptor (also known as CD279) is expressed on the surface of activated T cells. Its ligands, PD-L1 (B7-H1; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. Checkpoint inhibitors include, but are not limited to antibodies that block PD-1 (Nivolumab (BMS-936558 or MDX1106), CT-011, MK-3475), PD-L1 (MDX-1105 (BMS-936559), MPDL3280A, MSB0010718C), PD-L2 (rHIgM12B7), CTLA-4 (Ipilimumab (MDX-010), Tremelimumab (CP-675,206)), IDO, B7-H3 (MGA271), B7-H4, TIM3, LAG-3 (BMS-986016).

Human monoclonal antibodies to programmed death 1 (PD-1) and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

In some embodiments, the PDL1 inhibitor comprises an antibody that specifically binds PDL1, such as BMS-936559 (Bristol-Myers Squibb) or MPDL3280A (Roche). In some embodiments, the PD1 inhibitor comprises an antibody that specifically binds PD1, such as lambrolizumab (Merck), nivolumab (Bristol-Myers Squibb), or MEDI4736 (AstraZeneca). Human monoclonal antibodies to PD-1 and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies.

Anticancer agent comprising anti-PD-1 antibody or anti-PD-L1 antibody are described in U.S. Pat. No. 8,617,546, which is incorporated by reference for these antibodies.

The disclosed TLR9 Ligand Trap can be used in combination with a cancer immunotherapy. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Thus far, mAbs have been the biggest success story for immunotherapy; the top three best-selling anticancer drugs in 2012 were mAbs. Among them is rituximab (Rituxan, Genentech), which binds to the CD19 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

Generating optimal "killer" CD8 T cell responses also requires T cell receptor activation plus co-stimulation, which can be provided through ligation of tumor necrosis factor receptor family members, including OX40 (CD134) and 4-1BB (CD137). OX40 is of particular interest as treatment with an activating (agonist) anti-OX40 mAb augments T cell differentiation and cytolytic function leading to enhanced anti-tumor immunity against a variety of tumors.

In some embodiments, such an additional therapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine or cladribine.

In some embodiments, such an additional therapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In some embodiments, such an additional therapeutic agent may be selected from an anti-mitotic agent, such as taxanes, for instance docetaxel, and paclitaxel, and *vinca* alkaloids, for instance vindesine, vincristine, vinblastine, and vinorelbine.

In some embodiments, such an additional therapeutic agent may be selected from a topoisomerase inhibitor, such as topotecan or irinotecan, or a cytostatic drug, such as etoposide and teniposide.

In some embodiments, such an additional therapeutic agent may be selected from a growth factor inhibitor, such as an inhibitor of ErbBI (EGFR) (such as an EGFR antibody, e.g. zalutumumab, cetuximab, panitumumab or nimotuzumab or other EGFR inhibitors, such as gefitinib or erlotinib), another inhibitor of ErbB2 (HER2/neu) (such as a HER2 antibody, e.g. trastuzumab, trastuzumab-DM I or pertuzumab) or an inhibitor of both EGFR and HER2, such as lapatinib).

In some embodiments, such an additional therapeutic agent may be selected from a tyrosine kinase inhibitor, such as imatinib (Glivec, Gleevec ST1571) or lapatinib.

Therefore, in some embodiments, a disclosed antibody is used in combination with ofatumumab, zanolimumab, daratumumab, ranibizumab, nimotuzumab, panitumumab, hu806, daclizumab (Zenapax), basiliximab (Simulect), infliximab (Remicade), adalimumab (Humira), natalizumab (Tysabri), omalizumab (Xolair), efalizumab (Raptiva), and/or rituximab.

In some embodiments, a therapeutic agent for use in combination with a TLR9 Ligand Trap may be an anticancer cytokine, chemokine, or combination thereof. Examples of suitable cytokines and growth factors include IFNy, IL-2, IL-4, IL-6, IL-7, IL-10, IL-12, IL-13, IL-15, IL-18, IL-23, IL-24, IL-27, IL-28a, IL-28b, IL-29, KGF, IFNa (e.g., INFa2b), IFN, GM-CSF, CD40L, Flt3 ligand, stem cell factor, ancestim, and TNFa. Suitable chemokines may include Glu-Leu-Arg (ELR)-negative chemokines such as IP-10, MCP-3, MIG, and SDF-Ia from the human CXC and C—C chemokine families. Suitable cytokines include cytokine derivatives, cytokine variants, cytokine fragments, and cytokine fusion proteins.

In some embodiments, a therapeutic agent for use in combination with a TLR9 Ligand Trap may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. Nos. 6,440,735 and 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, and anti-sense Bcl-2.

In some embodiments, a therapeutic agent for use in combination with a TLR9 Ligand Trap may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxy-progesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane) or a hormone inhibitor (such as octreotide/sandostatin).

In some embodiments, a therapeutic agent for use in combination with TLR9 Ligand Trap may be an anti-cancer nucleic acid or an anti-cancer inhibitory RNA molecule.

Combined administration, as described above, may be simultaneous, separate, or sequential. For simultaneous administration the agents may be administered as one composition or as separate compositions, as appropriate.

In some embodiments, the disclosed TLR9 Ligand Trap is administered in combination with radiotherapy. Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

A number of embodiments of the invention have been described. Nevertheless, it will be understood that various modifications may be made without departing from the spirit and scope of the invention. Accordingly, other embodiments are within the scope of the following claims.

EXAMPLES

Example 1: TLR9-IgG4 Chimera Neutralizes Receptor Ligands to Suppress Inflammation and Pyroptosis in MDS In an effort to neutralize DAMPs and disrupt feed-forward inflammatory cycle, a chimeric protein fusing the external epitopes of TLR9 to the Fc domain of human IgG4 was designed to serve as a decoy receptor or ligand trap recognizing extracellular RNA:DNA hybrids (R-loops) and oxidized mitochondrial DNA. Neutralization of these important ligands that stimulate MDS HSPC is intended to suppress pyroptosis and the liberation of inflammatory cytokines directing ineffective hematopoiesis. Data shows that this TLR9-IgG4 chimera binds to its cognate TLR9 ligands (e.g., CpG) in a concentration-dependent fashion and augments colony forming capacity (CFC) in primary MDS bone marrow specimens when compared with IgG4 isotype control.

FIG. 1 is a schematic of an embodiment of the disclosed TLR9-IgG4 chimera ligand trap.

The TLR9 extracellular domain used has the amino acid sequence SEQ ID NO:1.

ELISA Design
1. Coat plate with IgG4 or TLR9-IgG4 overnight at 4 degree.
2. wash the plate with PBST.
3. Block with 1* Diluent at room temperature for 1 hour.
4. Wash the plate with PBST.
5. Add 0.25 uM 100 ul/well CpG-Biotin to each well at room temperature for 2 hours or 24 hours.
6. Wash the plate with PBST.
7. Add Avidin-HRP to the plate at room temperature for 30 minutes.
8. Wash the plate with PBST
9. add 1*TMB to each well at room temperature for 15 minutes.
10. Add stop solution
11. Read the plate at 450 nm, subtract the value of 570 nm from those of 450 nm and analyze data.

Figure 2:
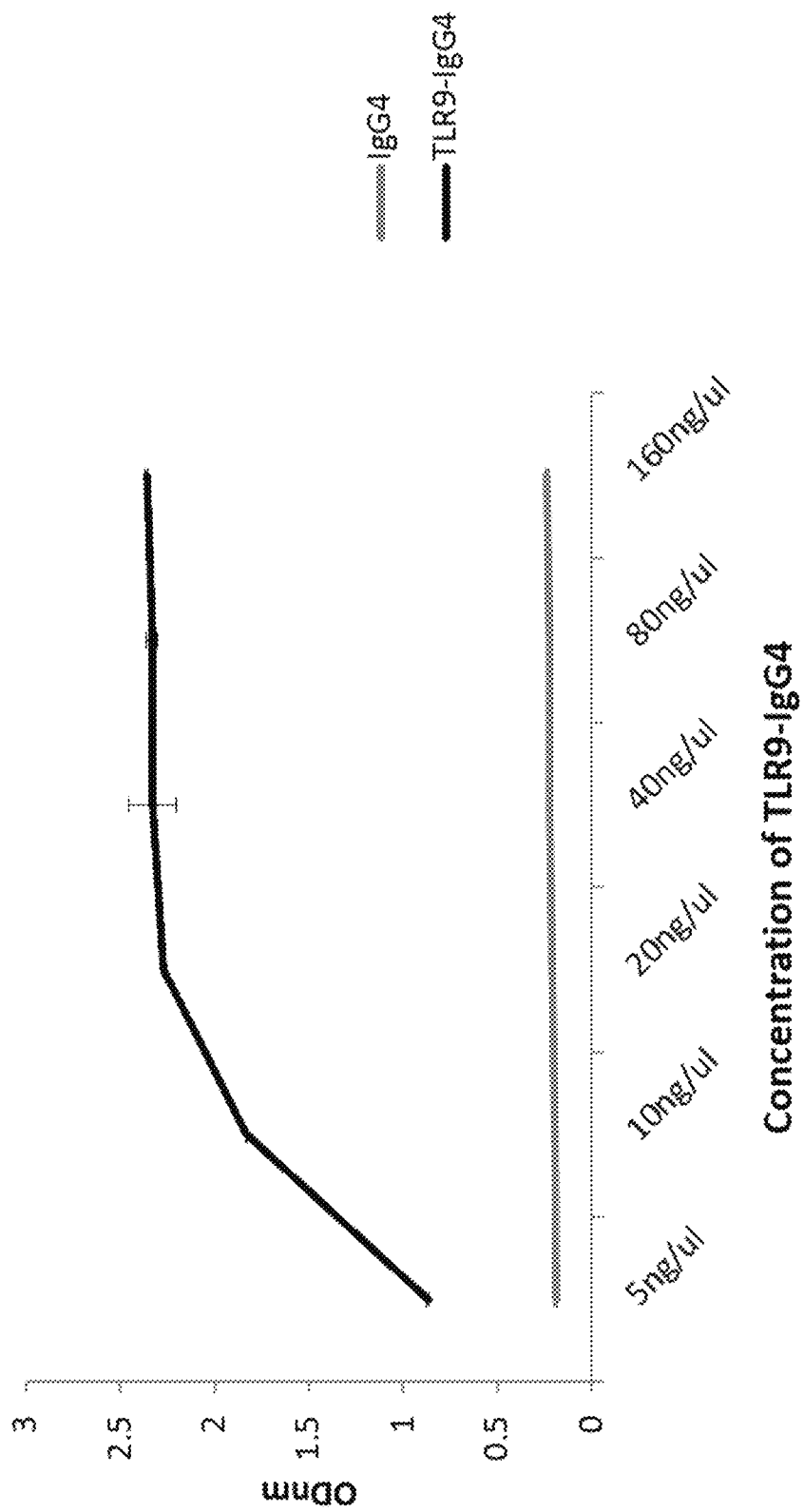
FIG. 2 is a graph showing concentration-dependent binding of CpG oligonucleotides to TLR9-IgG4.

FIG. 2 is a graph showing concentration-dependent binding of CpG oligonucleotides to TLR9-IgG4.

Figure 3:
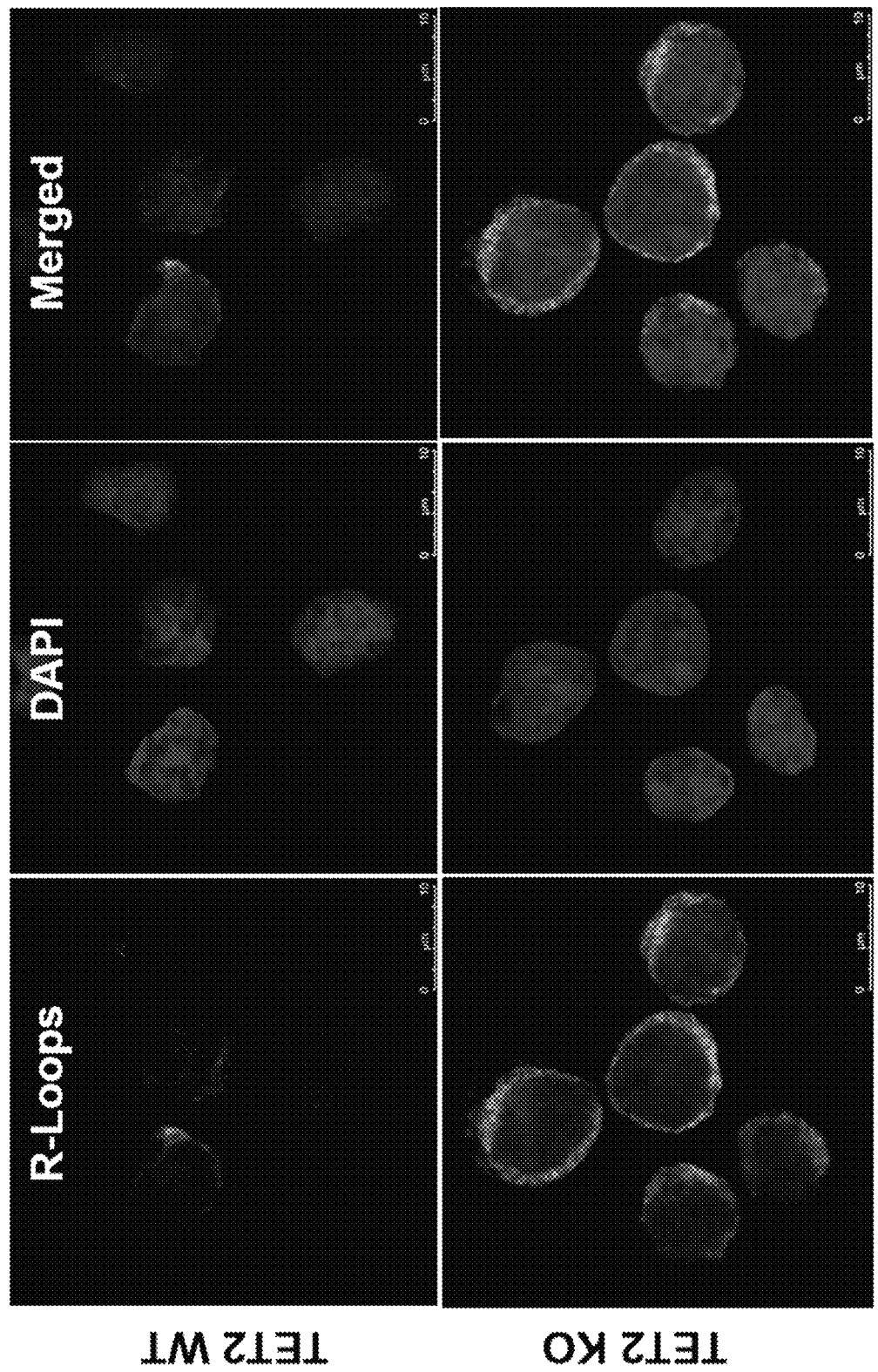
FIG. 3 is an image showing abundant DNA:RNA hybrids in Hoxb8 immortalized murine Tet2$^{-/-}$ HSPC.

FIG. 3 is an image showing abundant DNA:RNA hybrids in Hoxb8 immortalized murine Tet2$^{-/-}$ HSPC. By transducing mouse BM HSPC with an estrogen-regulated (ER)-Hoxb8 transgene7, we successfully immortalized HSPC from EZH2−/−, Tet2−/− and SRSF2-P95H/+ models and Wt animals. Nlrp3 IFM activation in TET2 KO HSPC is consistent with results of Fuster et. al. showing that Tet2 inactivation was sufficient to induce NLRP3 inflammasome activation in an atherosclerotic plaque model (Fuster J J, et al., Science 2017; 10.1126/science. aag1381 (Ahead of Print). Similarly, TET1 and TET2 are negative regulators of IL-1b. Consequently loss-of-function mutations in TET2 lead to increased IL-1b secretion, creating a proinflammatory bone marrow microenvironment that stimulates clonal hematopoiesis [Neves-Costa A, Moita L F. Mol Immunol. 2013; 54(3-4):264-2701.

Figure 4A:
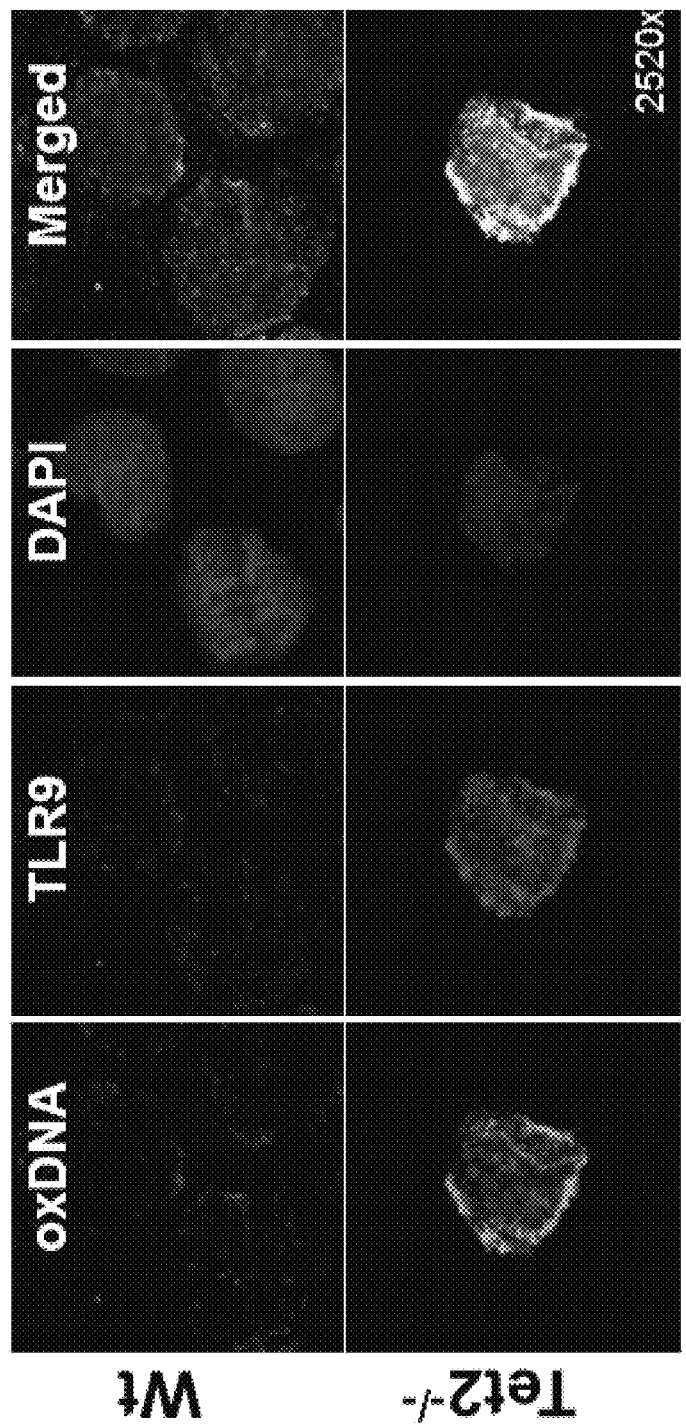
FIG. 4A to 4E show cytosolic oxidized mtDNA engages TLR9 in Tet2$^{-/-}$ murine HSPC.
Figures 4B, 4C:
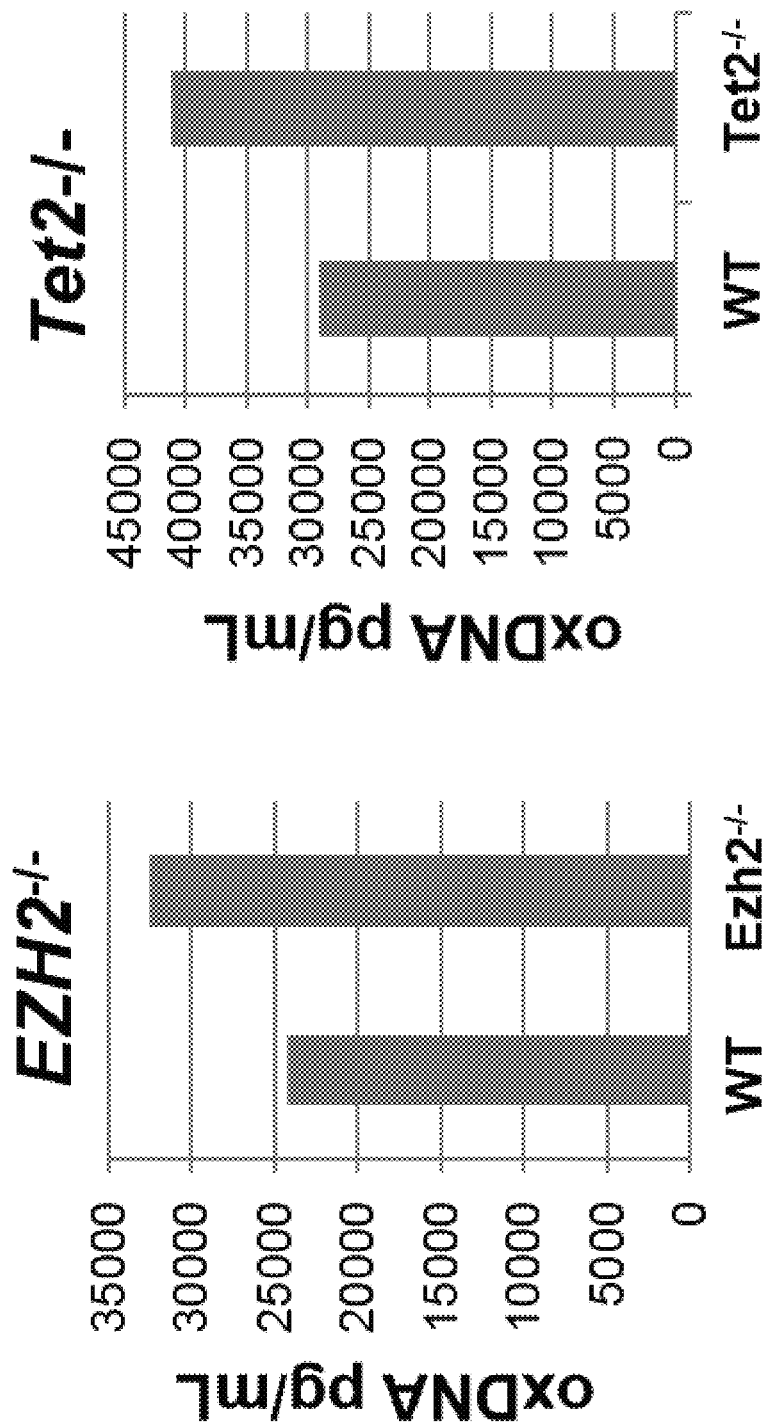
Figure 4E:
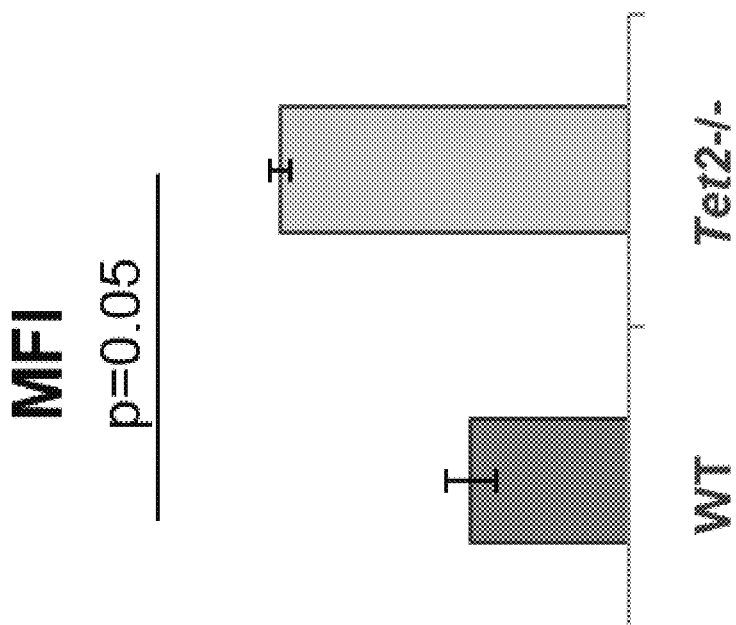
Figure 4D:
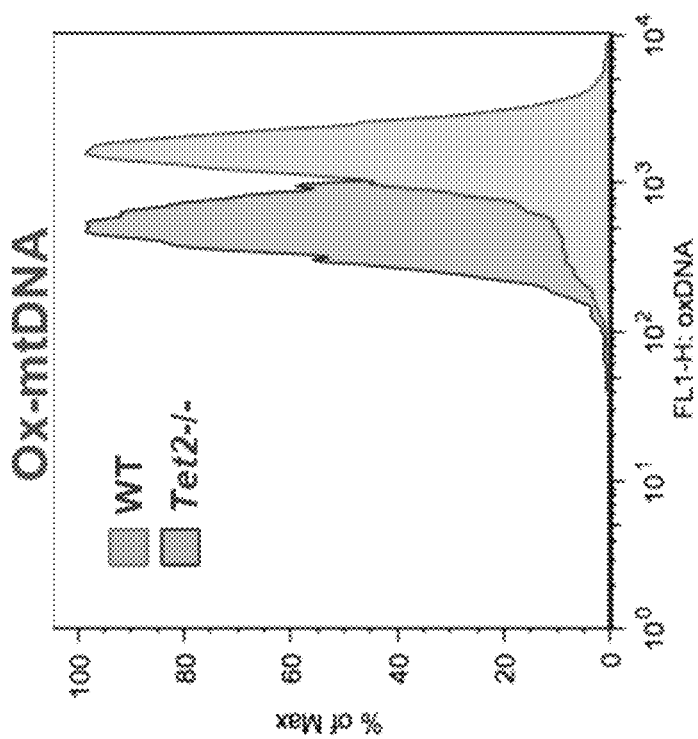

FIG. 4A to 4E show cytosolic oxidized mtDNA engages TLR9 in Tet2$^{-/-}$ murine HSPC. FIG. 4A is an image showing oxDNA, TLR9, and DAPI staining in wildtype and Tet2$^{-/-}$ murine HSPCs. FIGS. 4B and 4C contain bar graphs showing elevated OxDNA in supernatants of epigenetic EZH2$^{-/-}$ (FIG. 4B) and Tet2$^{-/-}$ (FIG. 4C) mutants. FIG. 4D is a graph showing ox-mtDNA in wildtype and Tet2$^{-/-}$ murine HSPCs. FIG. 4E is a bar graph showing MFI of wildtype and Tet2$^{-/-}$ murine HSPCs.

Figure 5:
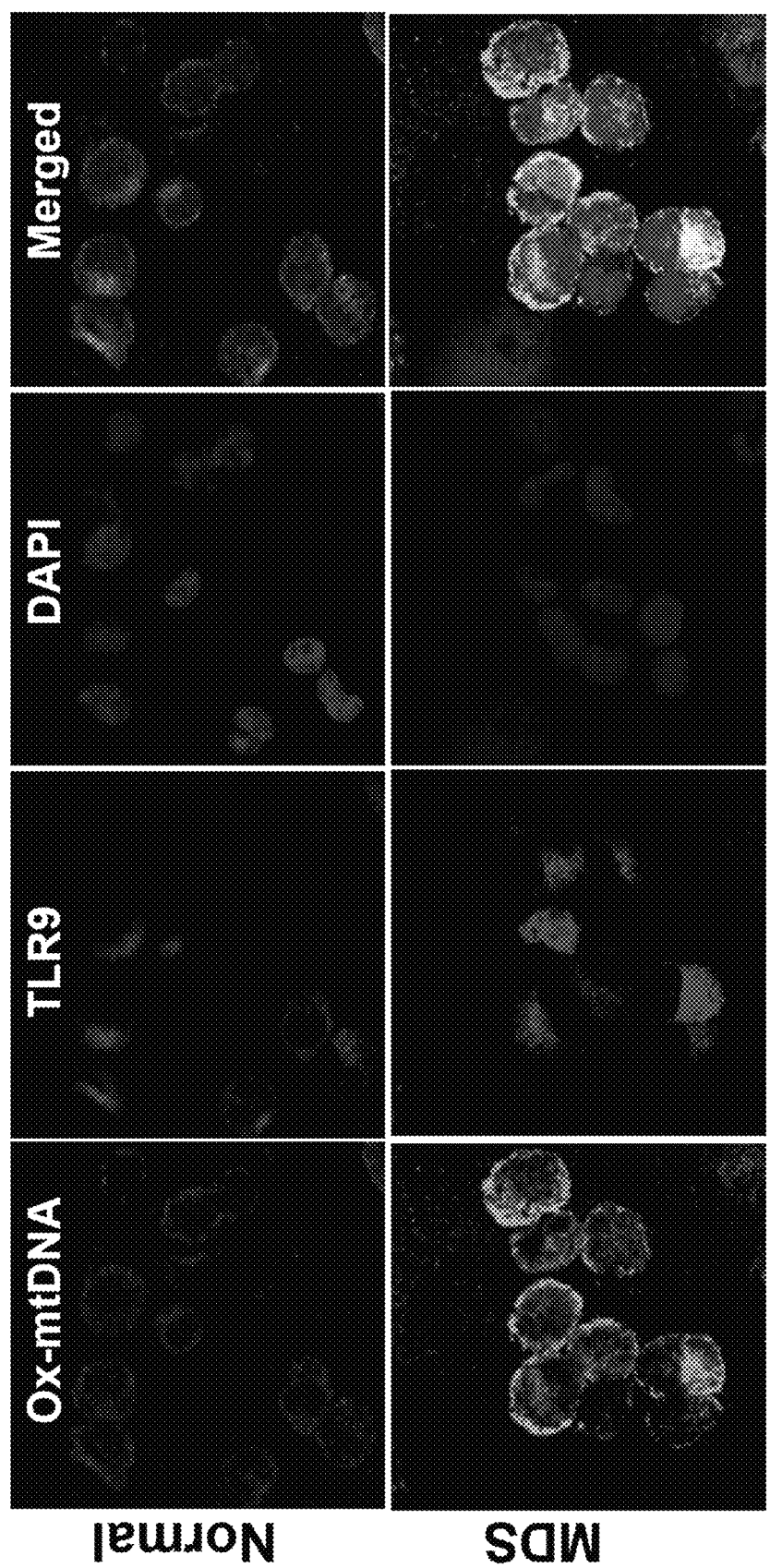
FIG. 5 is an image showing oxDNA, TLR9, and DAPI staining in normal and MDS HSPCs.

FIG. 5 is an image showing oxDNA, TLR9, and DAPI staining in normal and MDS HSPCs.

Figure 6A:
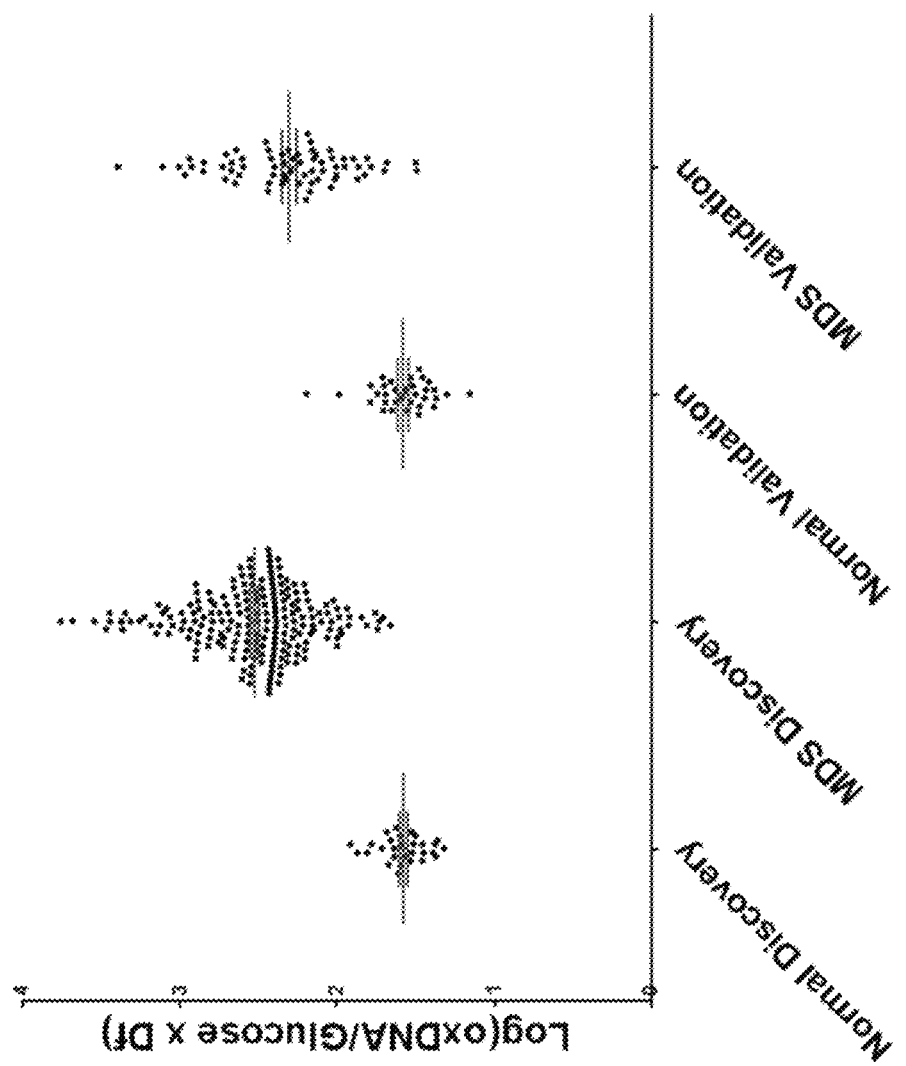
FIGS. 6A and 6B show quantitation of oxidized mitochondrial DNA in MDS patient plasma.
Figure 6B:
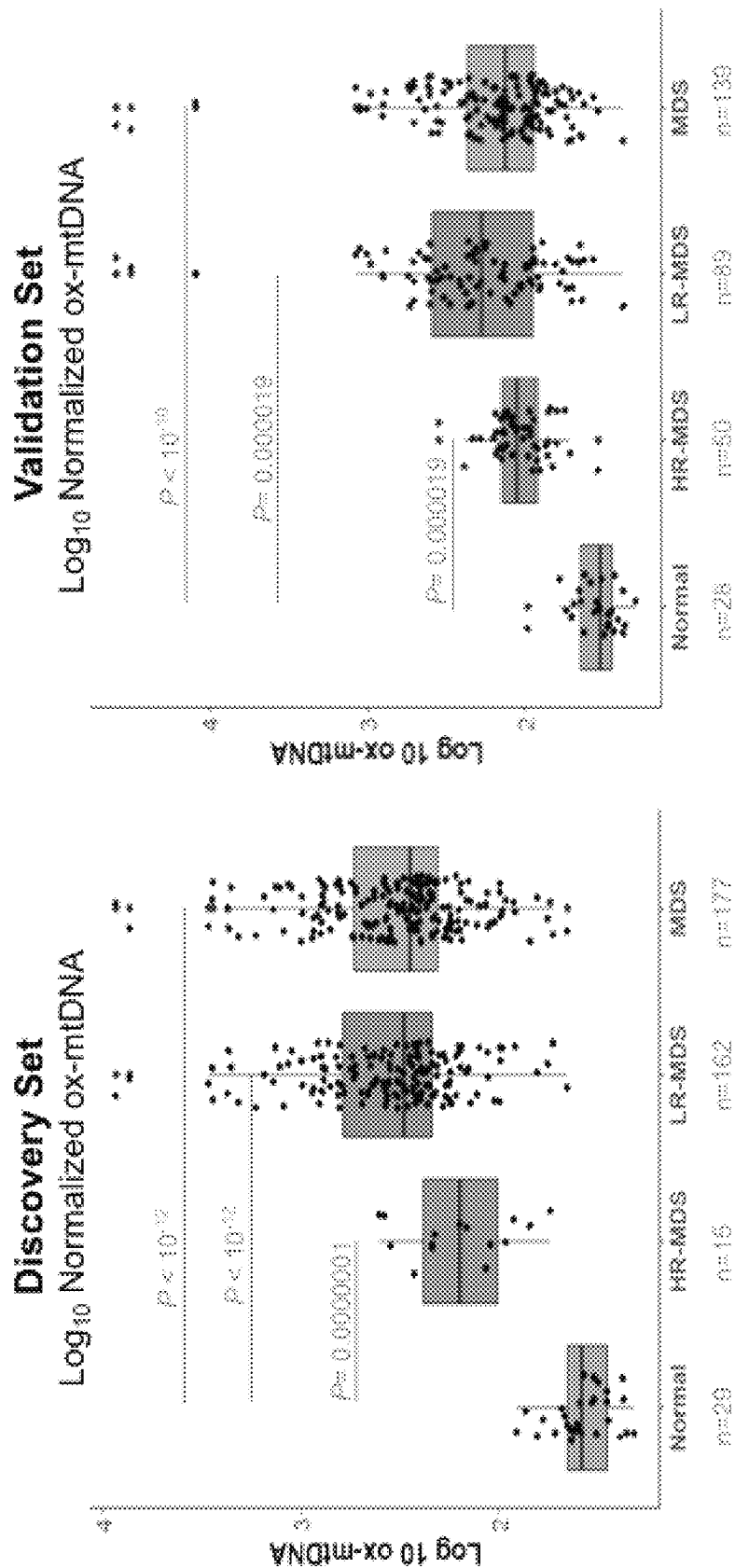

FIG. 6 is a plot showing quantitation of oxidized mitochondrial DNA in MDS patient plasma. Mitochondrial-membrane depolarization leads to release of oxidized mitochondrial DNA (ox-mtDNA) into the cytosol, where the hypomethylated CpG motifs present in mtDNA engage TLR9 and cGAS/STING. Further, ox-mtDNA has also been reported to directly bind Nlrp3 to initiate IFM assembly. Indeed, pyroptosis liberates mtDNA that can be detected in the peripheral blood. To assess circulating mtDNA in MDS, levels of plasma ox-mtDNA by ELISA were analyzed using an antibody that recognizes 8-hydroxy-2-deoxyguanosine (8-HPdG), the predominant form of ROS-induced oxidative lesions in mtDNA, in a test cohort of 207 MDS patients compared to 41 age-matched controls. Plasma ox-DNA was significantly elevated in MDS and was highest in lower risk (LR)-MDS versus high-risk (HR) disease or age-matched controls; these findings were confirmed in a separate validation cohort [n=67]

Figure 7:
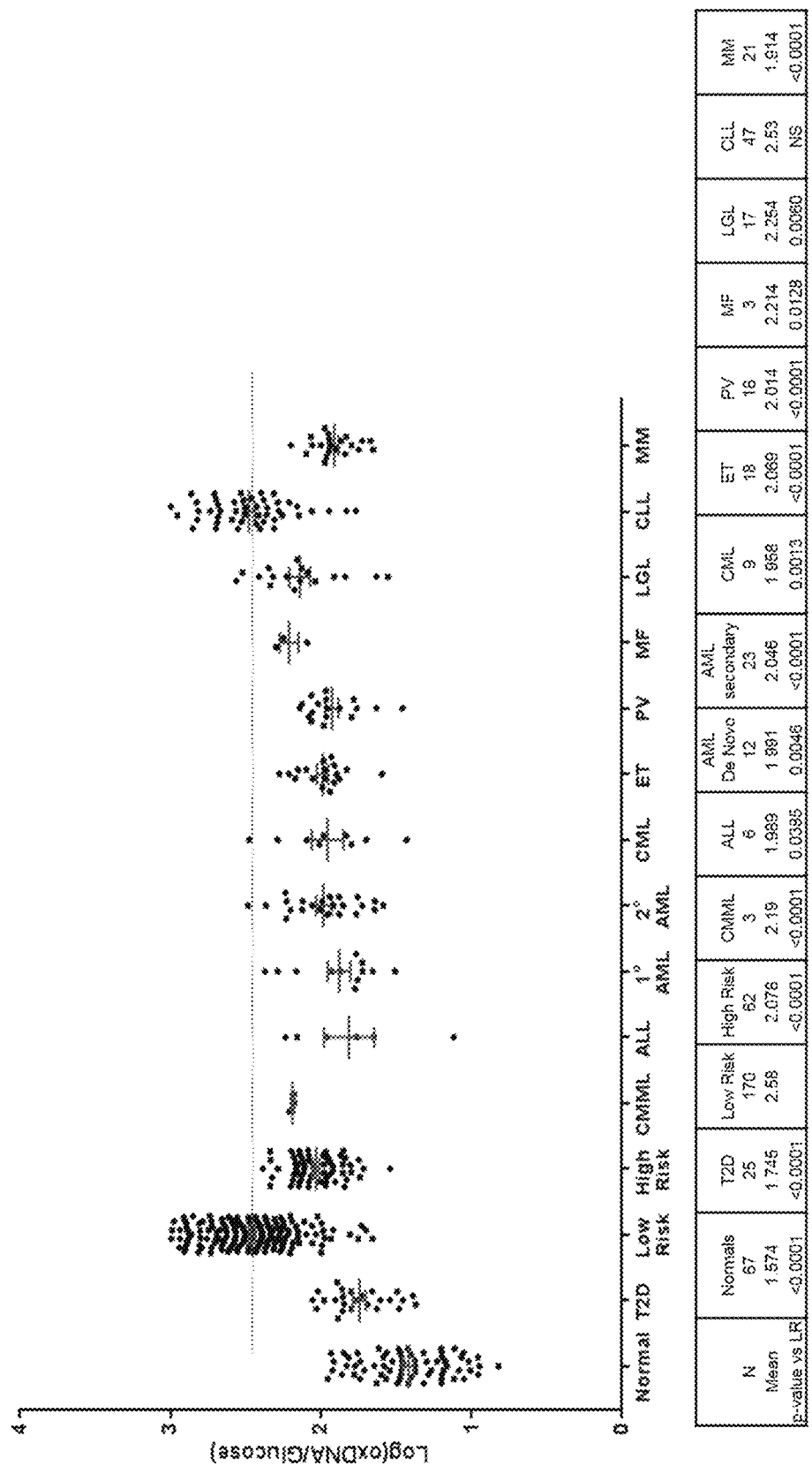
FIG. 7 is a plot showing plasma oxidized-mtDNA by disease type.

FIG. 7 is a plot showing plasma oxidized-mtDNA by disease type.

Figure 8:
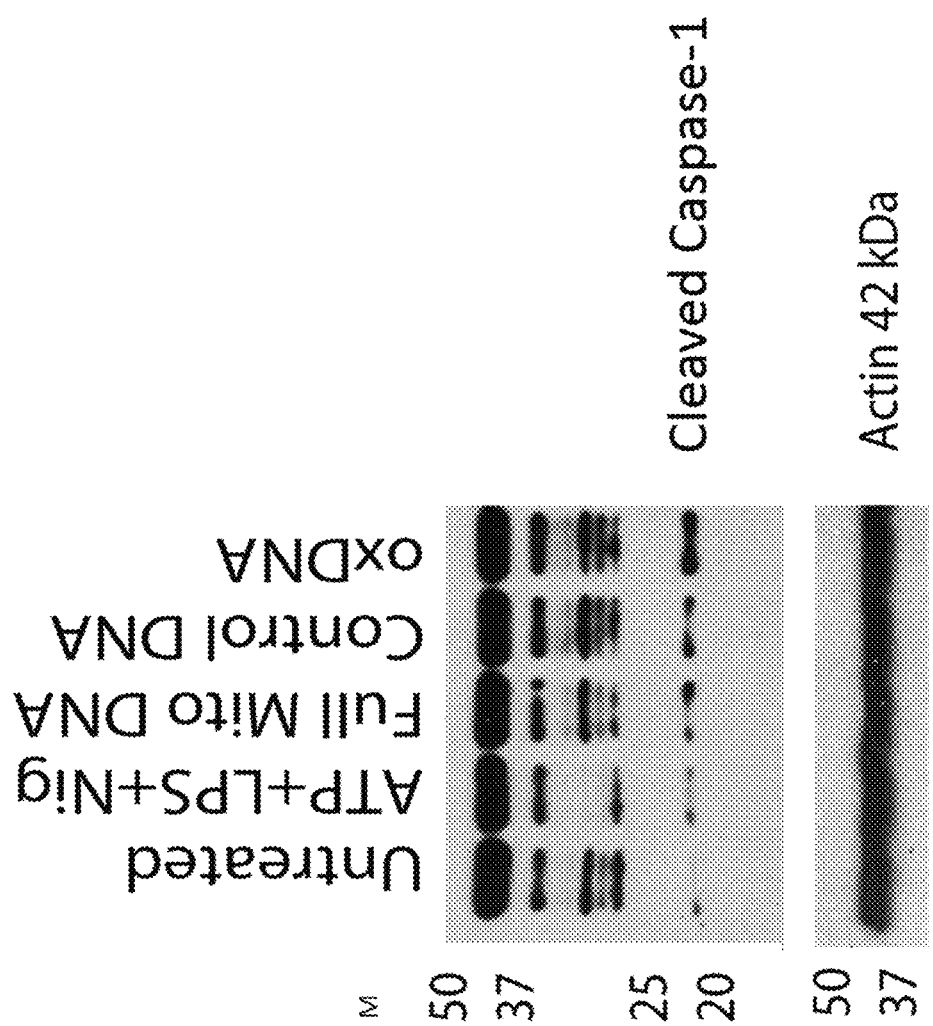
FIG. 8 is an image of a blot showing treatment of U937 cells with oxidized-mtDNA activates the Nlrp3 inflammasome.

FIG. 8 is an image of a blot showing treatment of U937 cells with oxidized-mtDNA activates the Nlrp3 inflammasome.

Figure 9:
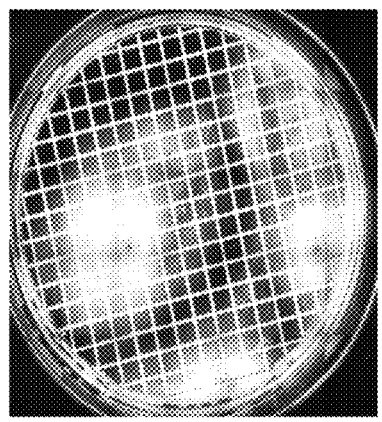
FIG. 9 are images showing TLR9-IgG4 promotes recovery of macroscopic multipotent progenitors in MDS BM specimens.
Figure 9:
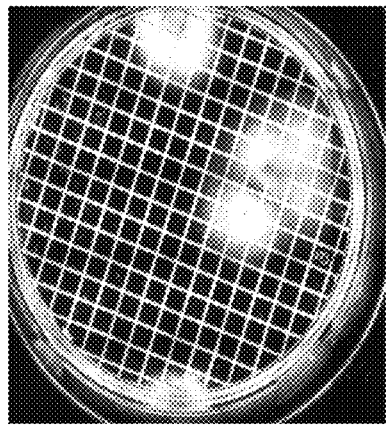
Figure 9:
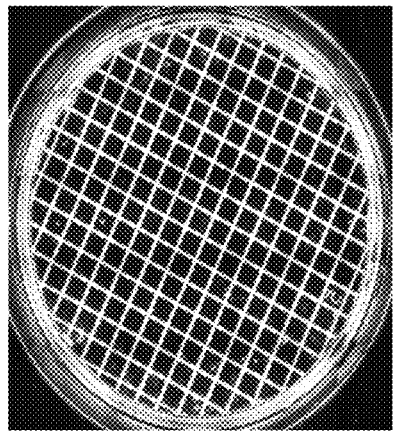
Figure 9:
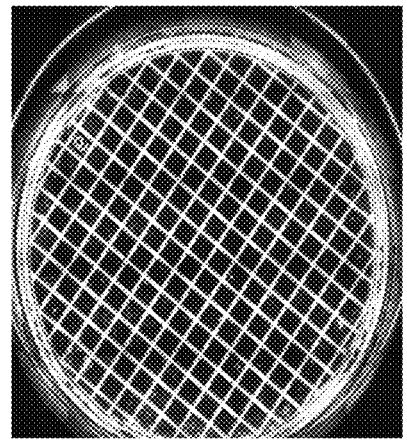

FIG. 9 are images showing TLR9-IgG4 promotes recovery of macroscopic multipotent progenitors in MDS BM specimens.

Figure 10:
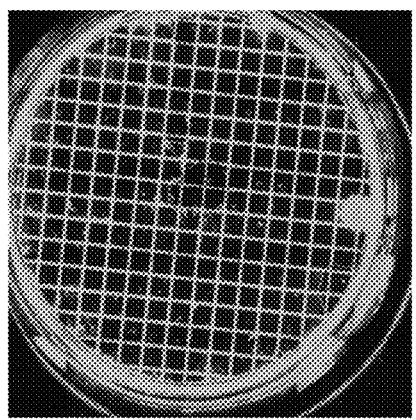
FIG. 10 are images showing TLR9-IgG4 promotes recovery of macroscopic multipotent progenitors in MDS BM specimens.
Figure 10:
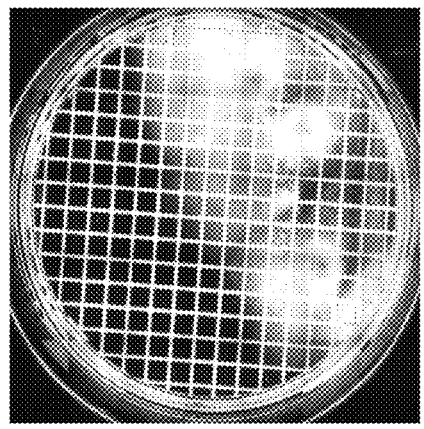
Figure 10:
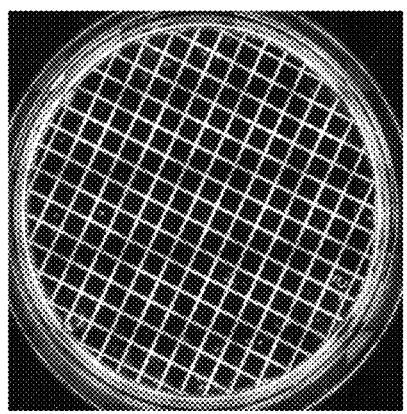
Figure 10:
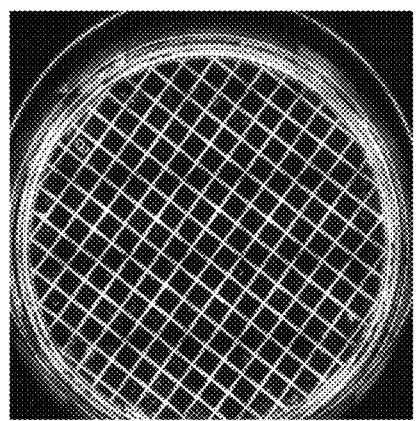

FIG. 10 are images showing TLR9-IgG4 promotes recovery of macroscopic multipotent progenitors in MDS BM specimens.

Figure 11A:
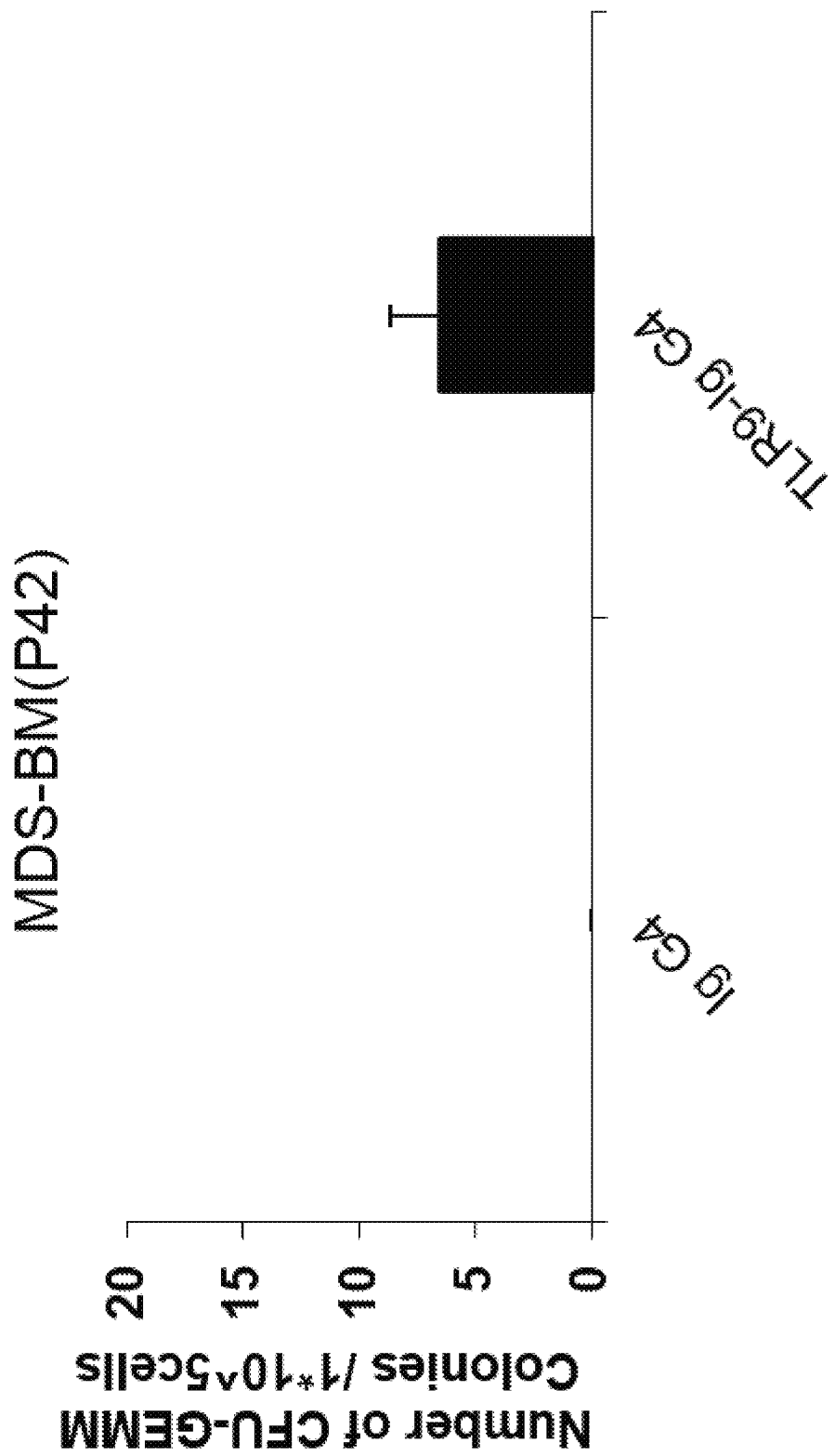
FIGS. 11A to 11D are bar graphs showing TLR9-IgG4 Ligand Trap promotes hematopoietic colony-forming capacity in MDS BM specimens P42 (FIG. 11A), P43 (FIG. 11B), P45 (FIG. 11C), and P46 (FIG. 11D).
Figure 11B:
Figure 11C:
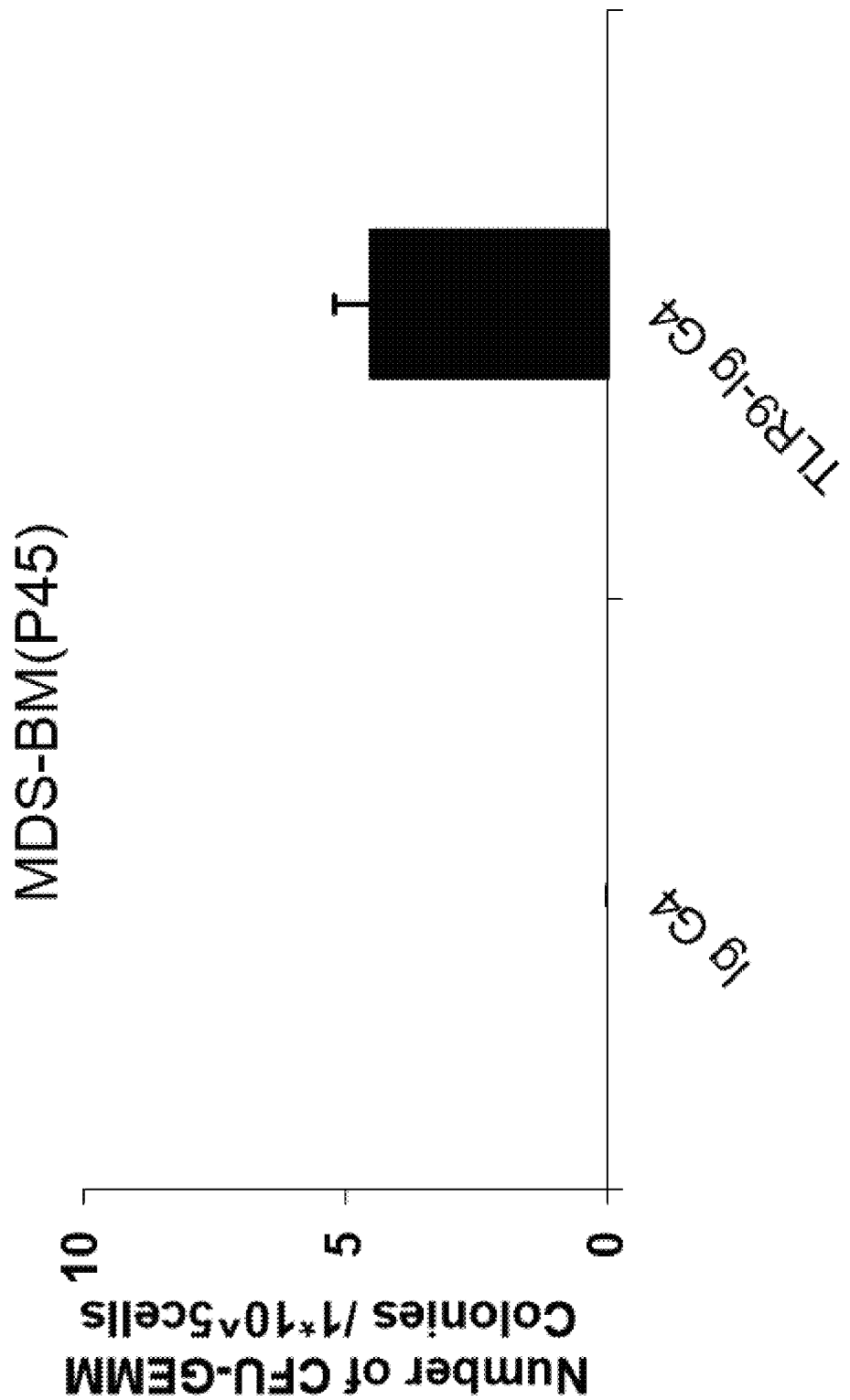
Figure 11D:
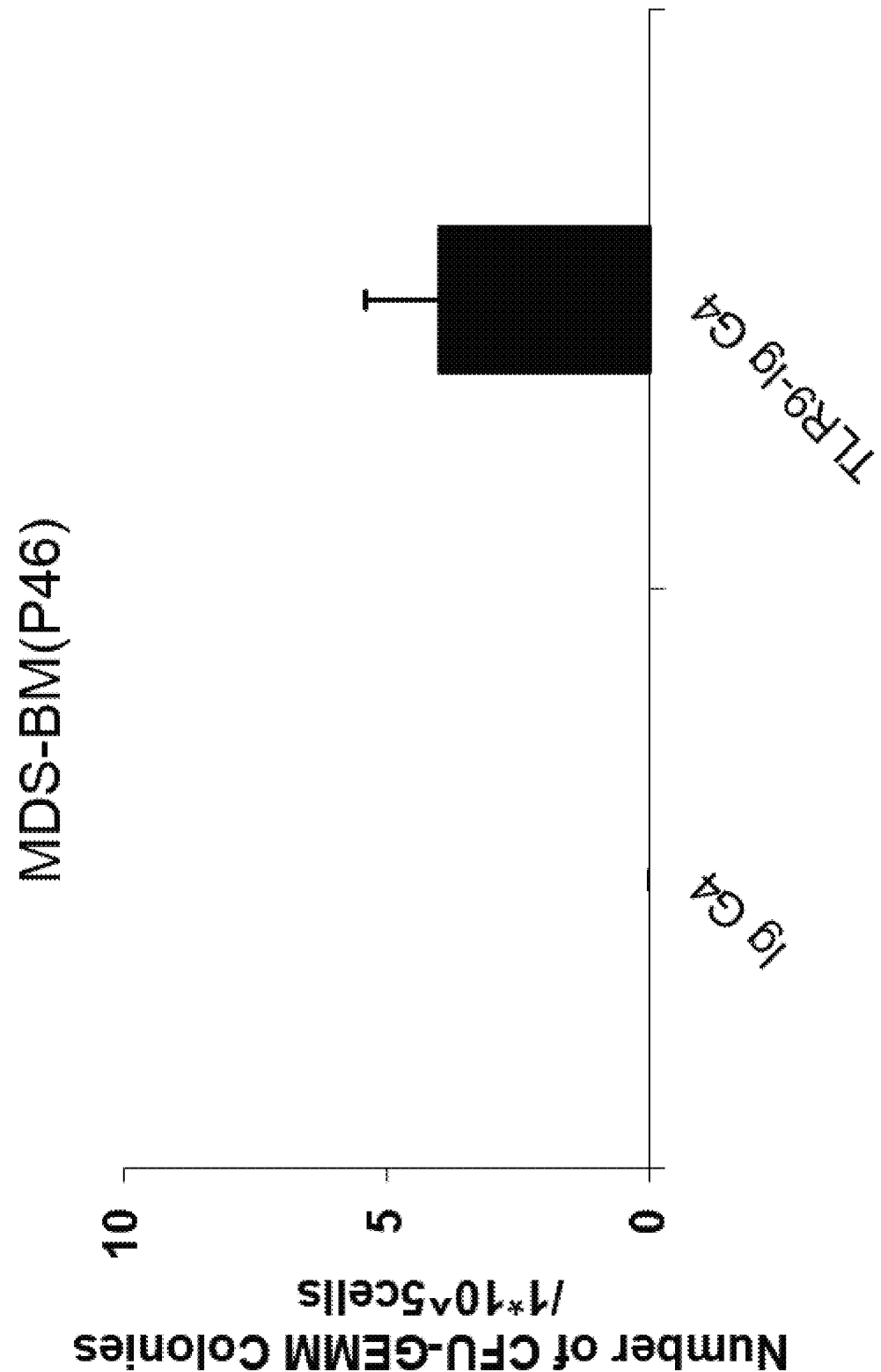

FIGS. 11A to 11D are bar graphs showing TLR9-IgG4 Ligand Trap promotes hematopoietic colony-forming capacity in MDS BM specimens P42 (FIG. 11A), P43 (FIG. 11B), P45 (FIG. 11C), and P46 (FIG. 11D).

Example 2: Oxidized Mitochondrial DNA is a Catalyst and Biomarker of Pyroptotic Cell Death in Myelodysplastic Syndromes Constitutive innate immune activation is a pathogenetic driver of Myelodysplastic Syndromes (MDS) that directs ineffective hematopoiesis by NLRP3 inflammasome (IFM) assembly and pyroptotic cell death. IFM activation involves recruitment of caspase-1 (casp1) through the adapter protein, ASC, to facilitate autocatalytic cleavage of the zymogen to its active form that is responsible for interleukin (IL)-1β maturation, membrane pore formation and pyroptosis. Oxidized mitochondrial DNA (ox-mtDNA) has been proposed to serve as an alarmin that can activate the IFM by interaction directly with NLRP3 or engagement by DNA sensors, Toll-like receptor 9 (TLR9) and Cyclic GMP-AMP synthase (cGAS). Upon cytolysis, ox-mtDNA is released, permitting interaction with pattern recognition receptors on neighboring cells (Grishman, Pediatric Research, 2012, Shimada, 2012, Immunity. Vollmer, 2004, Immunology). Investigate here is ox-mtDNA as an IFM-activator and pyroptotic biomarker in MDS.

Incubation of TLR9 expressing cell lines, SKM1 (high expresser) and U937 (moderate expresser) with 50 ng/mL ox-mtDNA (ND1 gene, amplified with oxidized guanosine) induced IFM activation evidenced by increased p-NFk8, casp1 and IL-1β cleavage, ASC oligomerization and liberation of ASC specks. Direct interaction of ox-mtDNA with NLRP3 was confirmed by NLRP3 immunoprecipitation followed by probing for mtDNA using ND1 and CYTB specific primers and GAPDH primers as negative genomic control; mtDNA oxidation status was confirmed by dot blot. Furthermore, significantly increased expression of interferon stimulated genes (ISG) was seen in MDS bone marrow (BM) specimens (p50.01) compared to normal donors indicating TLR9 and/or cGAS activation. Ox-mtDNA engagement of TLR9 and cGAS was confirmed in MDS specimens by IF colocalization with corresponding IFM activation, as well as in MDS somatic gene mutation murine models (Tet2, SRSF2, U2AF) vs. Wt controls. Evaluation of surface TLR9 by flow cytometry showed significantly increased membrane expression in MDS CD34+ BMMC (n=4) vs. healthy donors (n=13) ($p<0.05$), suggesting priming for enhanced sensitivity to ox-mtDNA. Concentrations of ox-mtDNA in supernatants from THP1 (N=5, p=0.0547), U937 (N=3, p=0.0637), and SKM1 (N=3, p=0.028) cells confirmed extracellular release after L/A/N-induced pyroptosis. ox-mtDNA concentrations were next investigated in peripheral blood plasma from MDS patients by ELISA. Glucose adjusted, ox-mtDNA levels were significantly increased in 177 MDS cases compared to 29 healthy donors ($p<0.0001$), which was validated in an independent cohort of 154 MDS cases and 34 healthy donors ($p<0.0001$). Ox-mtDNA was higher in lower risk (LR) compared to higher risk MDS ($p<0.0001$) consistent with greater pyroptotic cell fraction in LR-MDS. Further, there was a direct correlation between ox-mtDNA (N=124) and known MDS IFM-activating alarmins S100A9 (r 2=0.570), S100A8 (r 2=0.555), and percentage of ASC specks (r 2=0.483) ($p<0.0001$ for all), demonstrating specificity of ox-mtDNA as a biomarker for the magnitude of medullary pyroptosis in MDS. Importantly, compared to other hematological malignancies, plasma ox-mtDNA was significantly increased in LR-MDS (n=162) compared to ALL (n=7), de novo (n=20) and secondary AML (n=18), CML (n=8), CMML (n=18), LGL (n=19), MF (n=12), ET (n=20), PV (n=20), MM (n=18), and type 2 diabetes (n=25) where IFM activation promotes insulin resistance ($p≤0.036$). There was no significant difference in oxDNA concentrations between MDS and CLL (n=50), which is reported to have high ox-mtDNA levels associated with genomic abnormalities (Collado, 2014, Biomed Res Int.). ROC/AUC analysis demonstrated that ox-mtDNA was an MDS pyroptosis-specific biomarker when compared to healthy donors (AUC=0.929). Similarly, a 5-fold cross-validation (k=5) repeated 30 times to compare MDS cases to non-MDS hematological malignancies (excluding CLL), similarly confirmed biomarker specificity (AUC=0.877).

Collectively, these data indicate that ox-mtDNA both directly engages NLRP3 and the DNA sensors TLR9/cGAS to induce IFM activation and pyroptosis, creating a feed forward inflammatory cascade that extends to neighboring cells. Ox-mtDNA can serve as a biomarker and companion diagnostic for pyroptosis execution in MDS.

Example 3: Oxidized Mitochondrial DNA is a Catalyst and Biomarker of Pyroptotic Cell Death in Myelodysplastic Syndromes Constitutive innate immune activation is a pathogenic driver of Myelodysplastic Syndromes (MDS) that directs ineffective hematopoiesis by NLRP3 inflammasome (IFM) assembly and pyroptotic cell death. IFM activation involves recruitment of caspase-1 (casp1) through the adapter protein, ASC, to facilitate autocatalytic cleavage of the zymogen to its active form that is responsible for interleukin (IL)-1β maturation, membrane pore formation and pyroptosis. Oxidized mitochondrial DNA (ox-mtDNA) has been proposed to serve as an alarmin that can activate the IFM by engagement of DNA sensors. Cytosolic oxDNA interacts with pattern recognition receptors Toll-like receptor 9 (TLR9) and Cyclic GMP-AMP synthase (cGAS) resulting in downstream activation of interferon stimulated genes and the IFM. Upon cytolysis, ox-mtDNA is released, permitting interaction with pattern recognition receptors on neighboring cells (Grishman, Pediatric Research, 2012, Shimada, 2012, Immunity. Vollmer, 2004, Immunology). Here, ox-mtDNA was investigate as an IFM-activator and pyroptotic biomarker in MDS.

Methods

Normal peripheral blood (PB) plasma from was obtained from Florida Blood Services. MDS patient plasma samples were acquired on IRB approved protocols and stratified according to the International Prognostic Scoring System (IPSS). LR is IPSS<1 and HR is IPSS 1.5.

Plasma oxDNA was quantified using the DNA/RNA Oxidative Damage ELISA Kit (#589320, Cayman Chemical). Plasma glucose concentration was measured using Glucose Colorimetric Assay Kit (#10009582, Cayman Chemical). S100A8 and S100A9 were measured using CircuLex S100A8/MRP8 (CY-8061) and CircuLex S100A9/MRP14 (CY-8062) ELISA kits (MBL International Corporation).

IF was performed on cytospun BM-MNC stained with Anti-DNA/RNA Damage antibody [15A3] (FITC) (ab183393), Anti-TLR9 antibody (13674T), Anti-cGAS antibody (15102S), Alexa 647 Goat Anti-Rabbit (Fisher A21446). DAPI ProLong Gold antifade reagent (Fisher P36931) and visualized on a Leica Confocal SP8.

Results

Figure 12A:
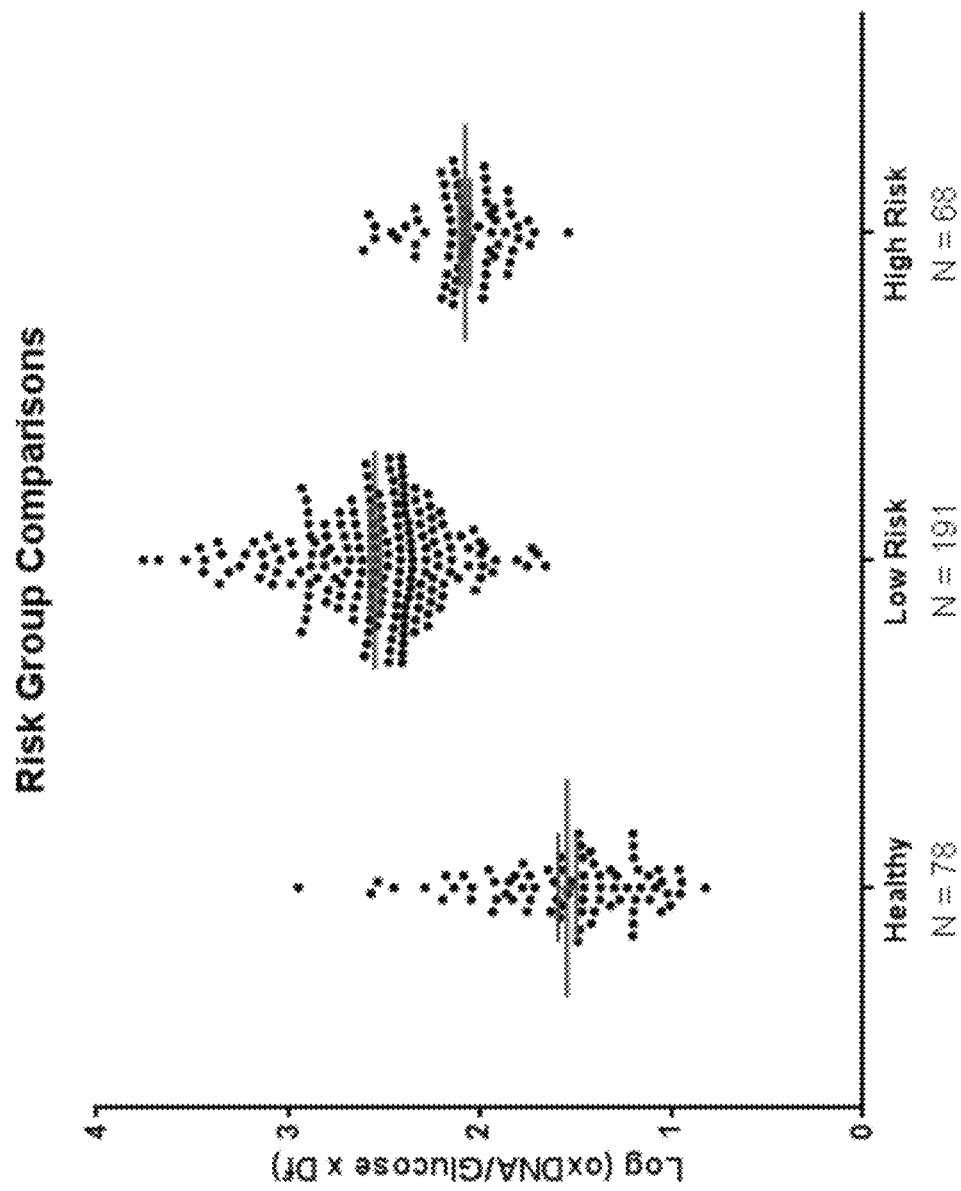
FIGS. 12A to 12E show oxidized DNA increased in MDS.
Figure 12B:
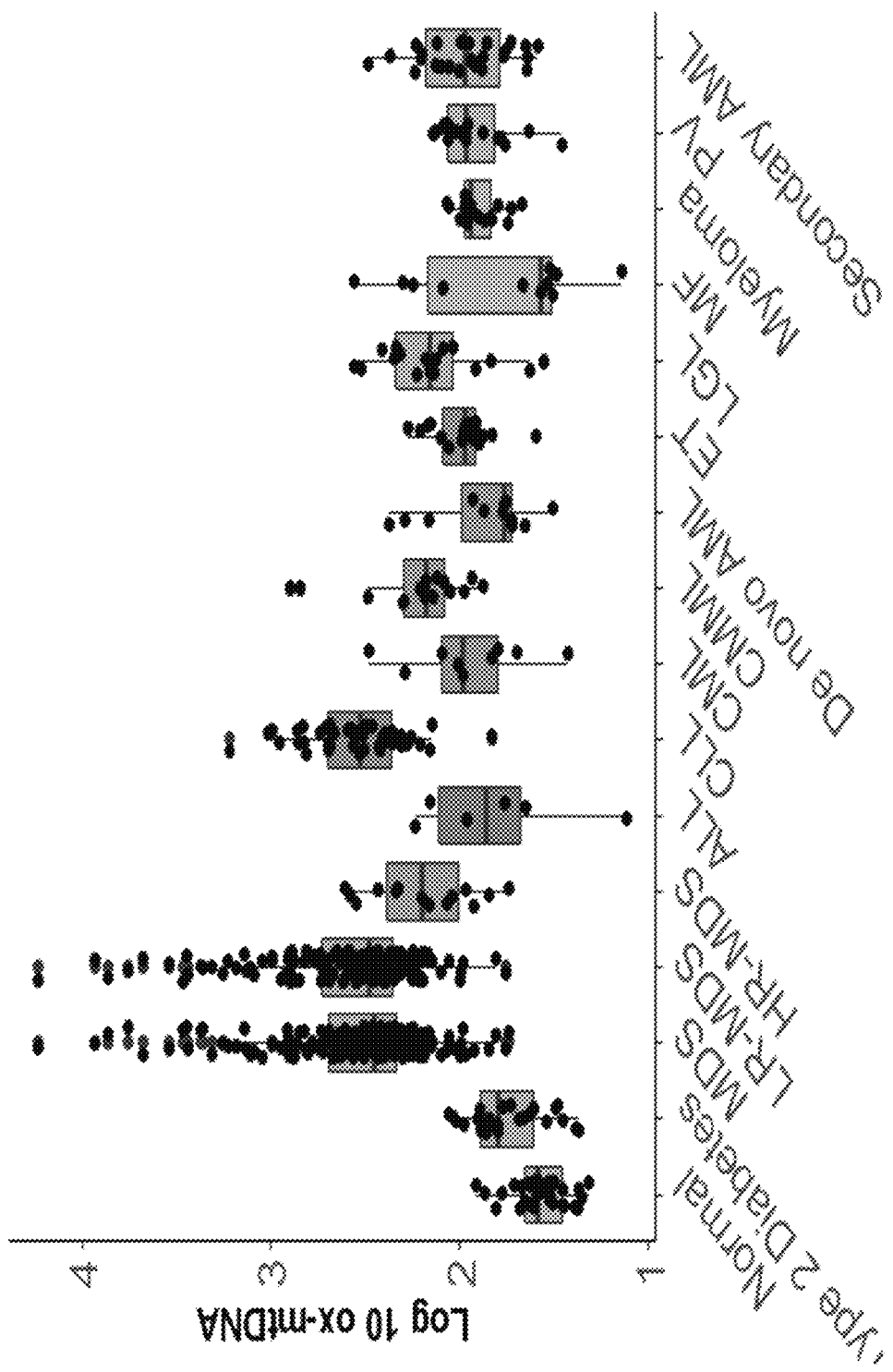
Figure 12C:
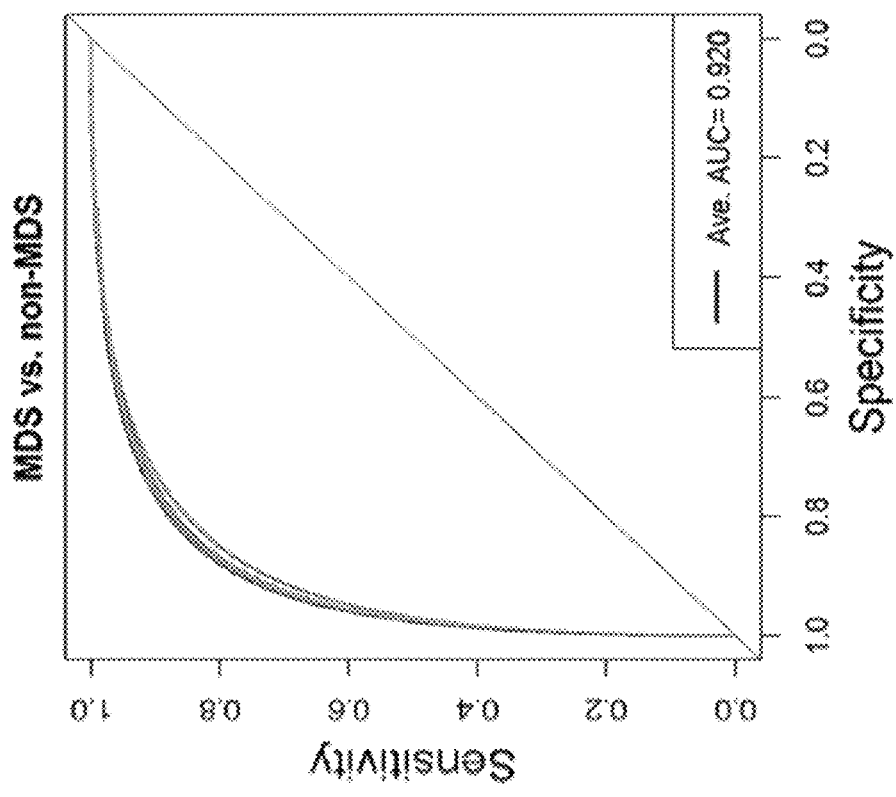
Figure 12C:
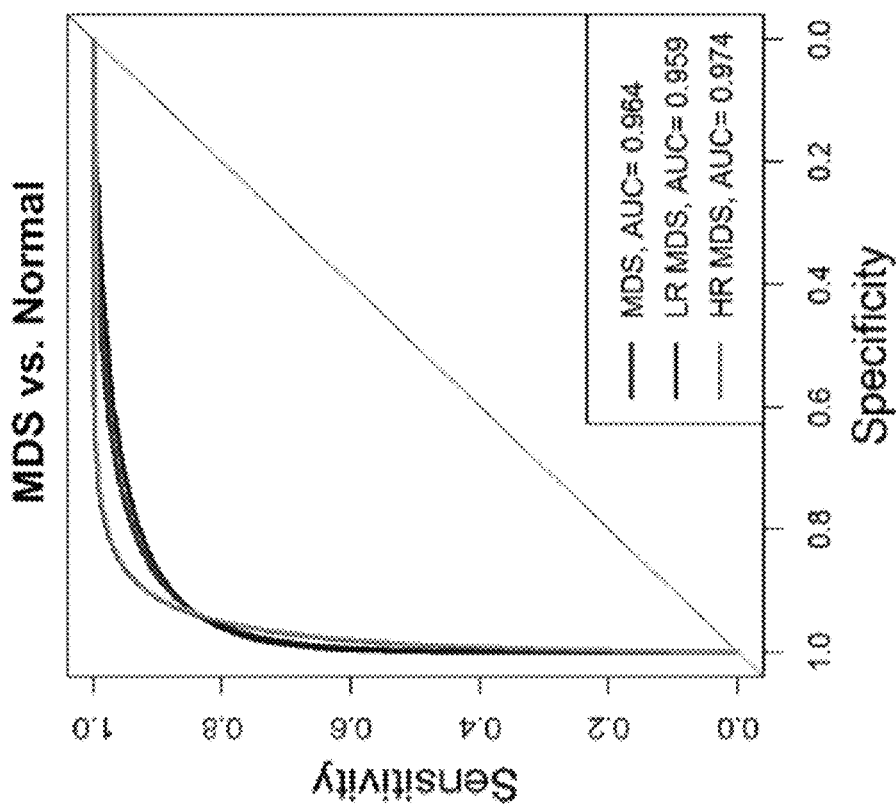
Figure 12D:
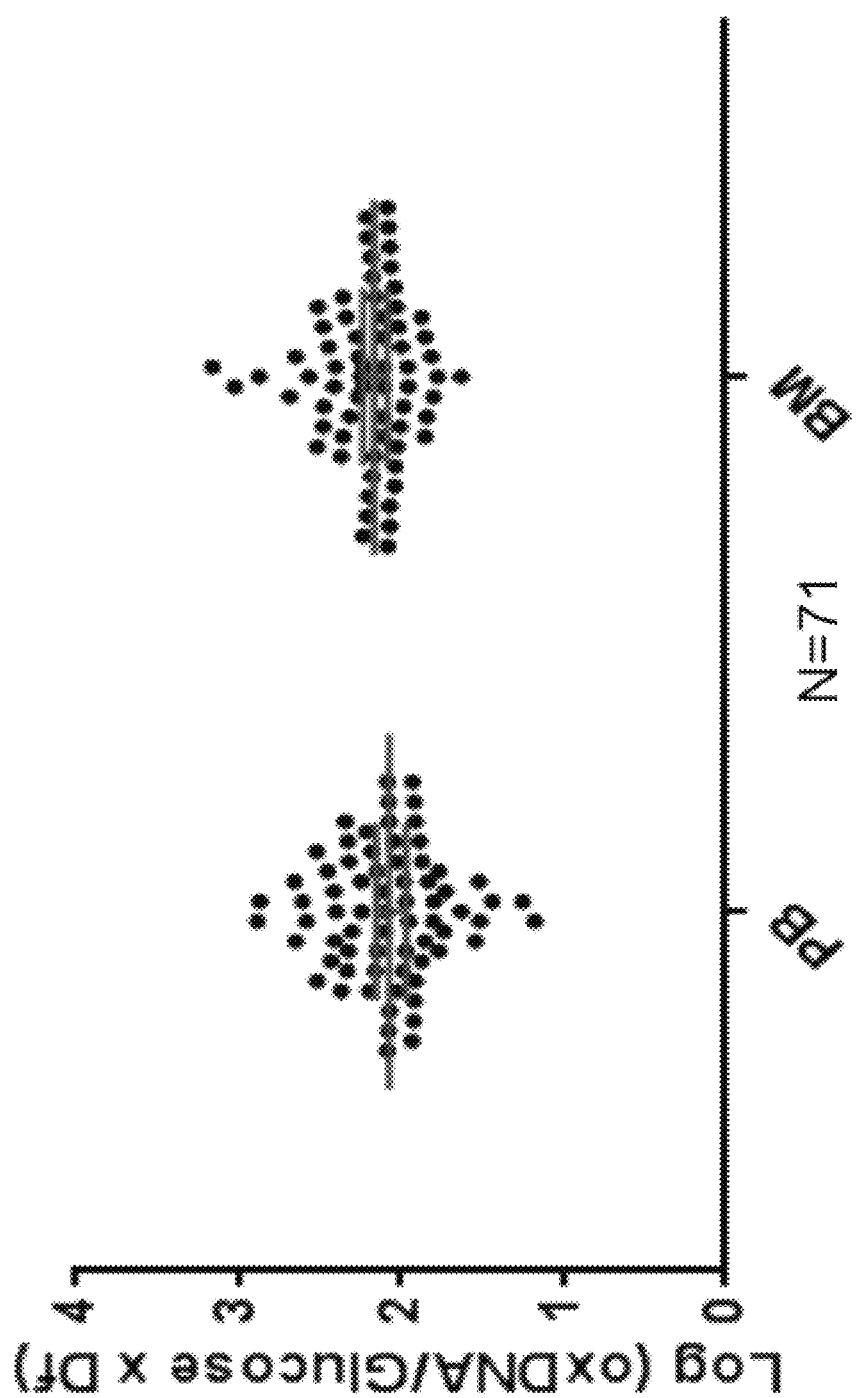
Figure 12E:
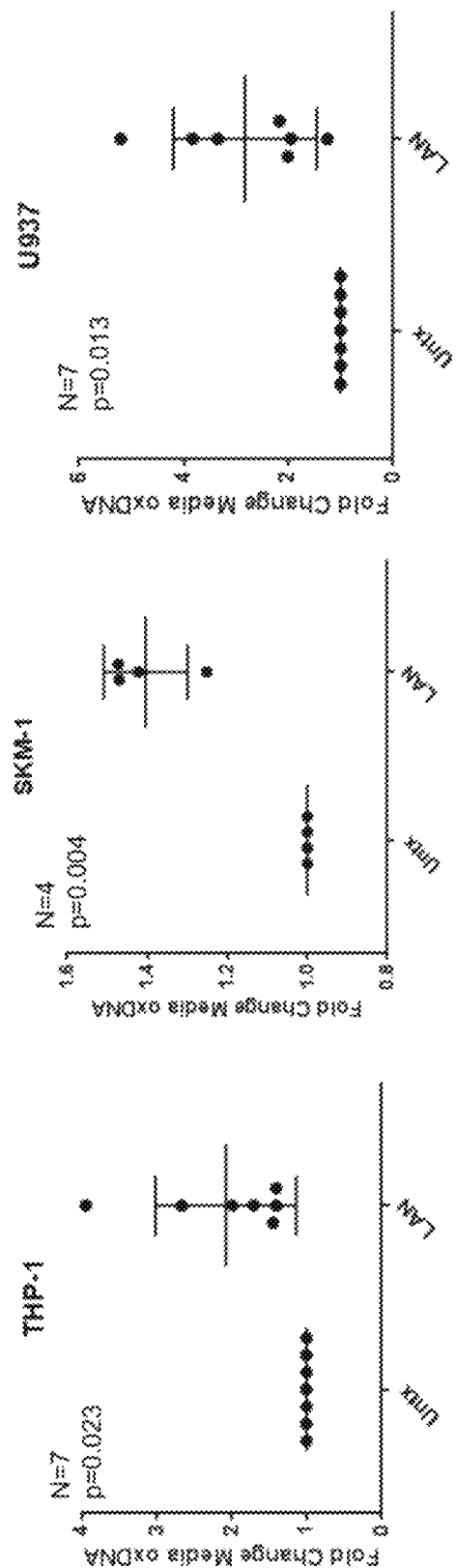

FIGS. 12A to 12E show oxidized DNA increased in MDS. FIGS. 12A and 12B show OxDNA levels are significantly higher in LR patients compared to HR patients (FIG. 12A) and all other hematologic malignancies ($p≤0.03$) except CLL which has been previously shown to have increased oxDNA in relation to unfavorable cytogenetics (FIG. 12B). FIG. 12C shows OxDNA demonstrates a AUC/ROC of 0.964 with a specificity of 0.777 and sensitivity of 0.95 demonstrating the utility of oxDNA as a strong biomarker for MDS. FIG. 12D shows OxDNA is slightly increased in LR patient bone marrow compared to peripheral blood. FIG. 12E shows OxDNA is significantly released as a result of NLRP3 inflammasome activation.

Figure 13A:
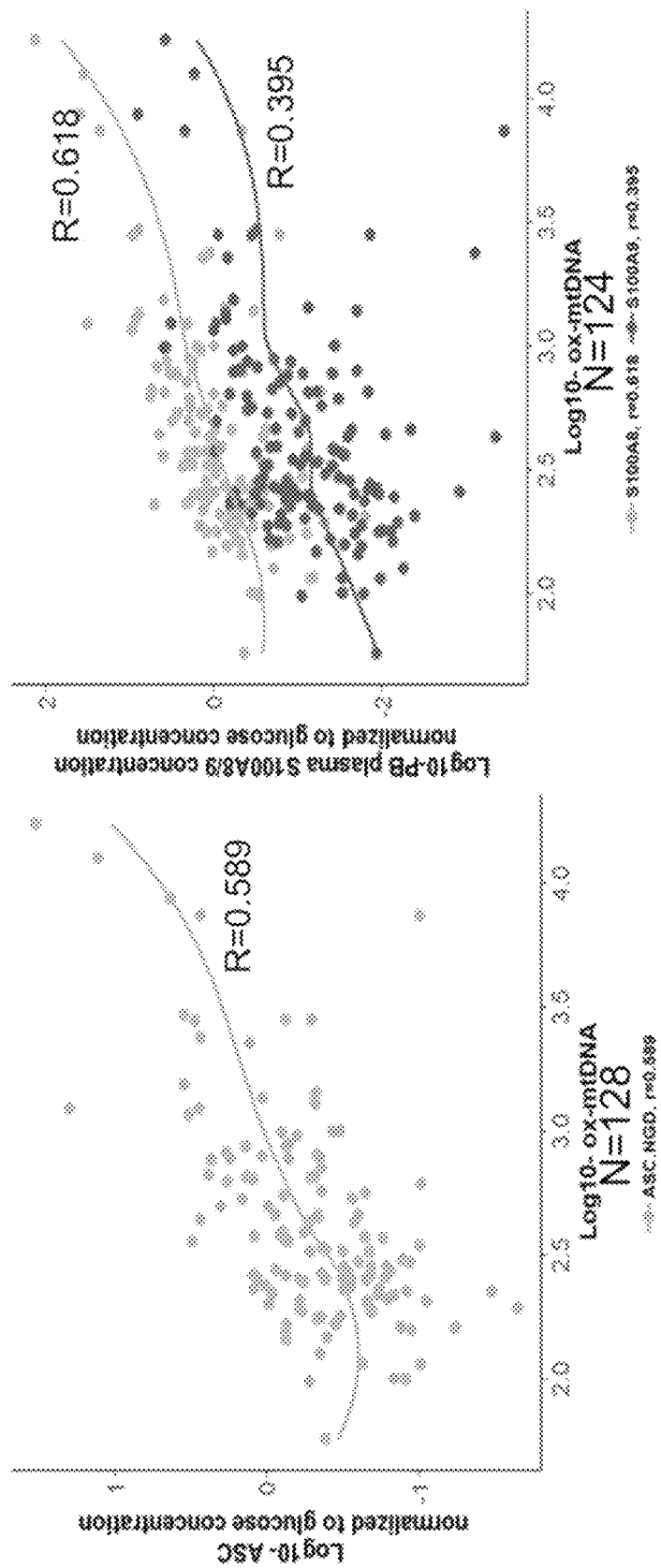
FIGS. 13A to 13E show oxidized-mtDNA as a DAMP in MDS.
Figure 13B:
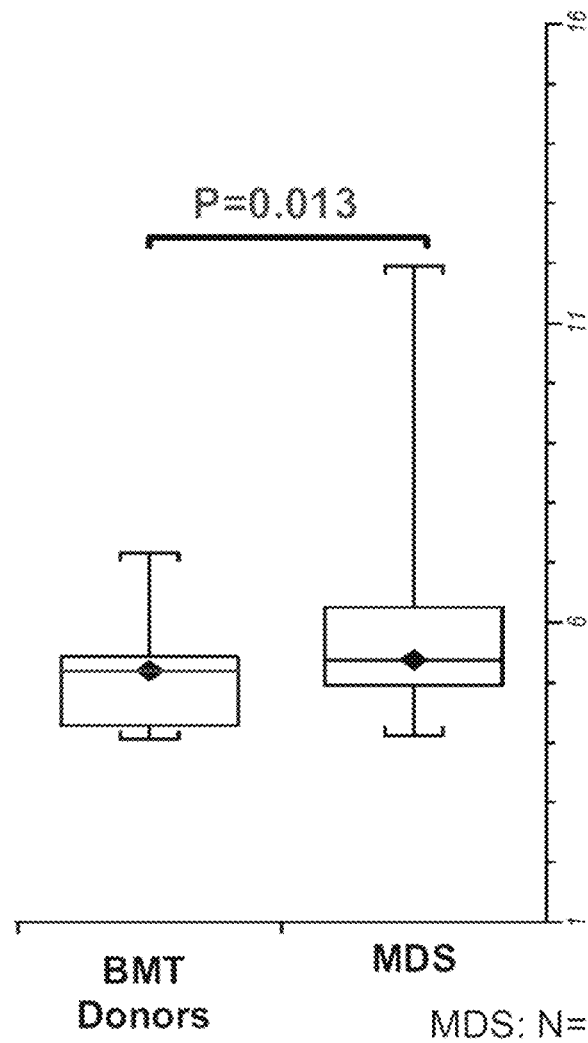
Figure 13B:
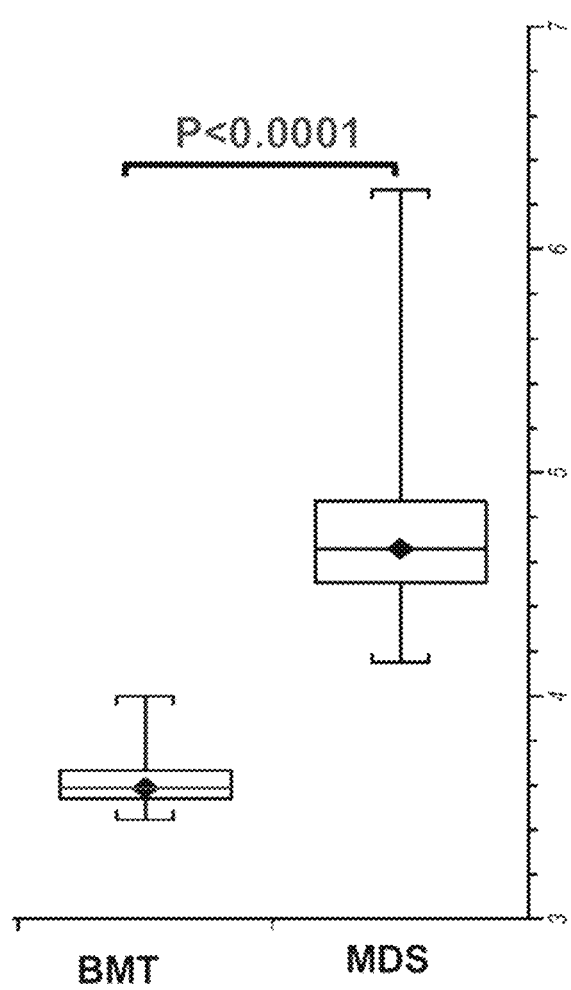
Figures 13C, 13D:
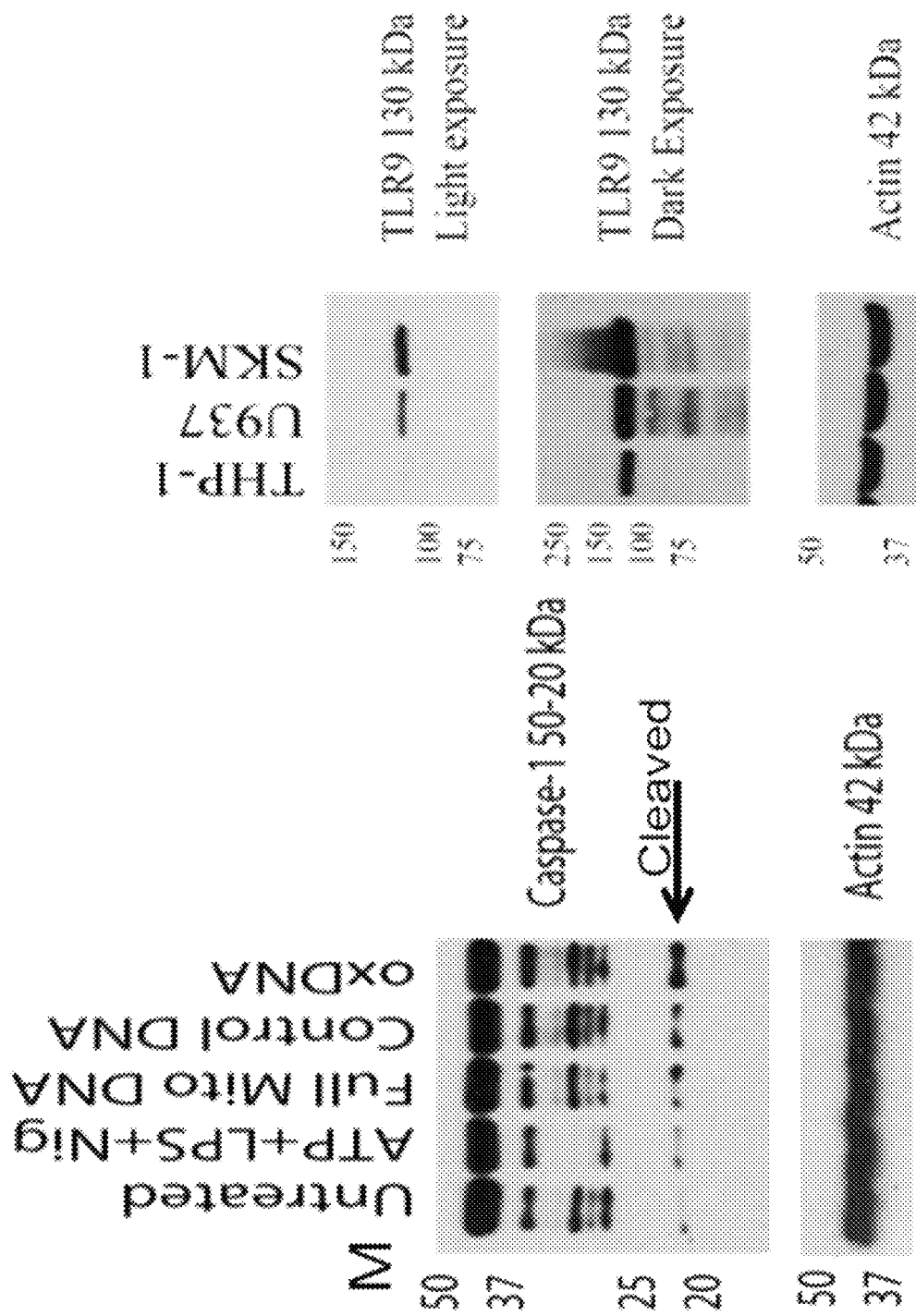
Figure 13E:
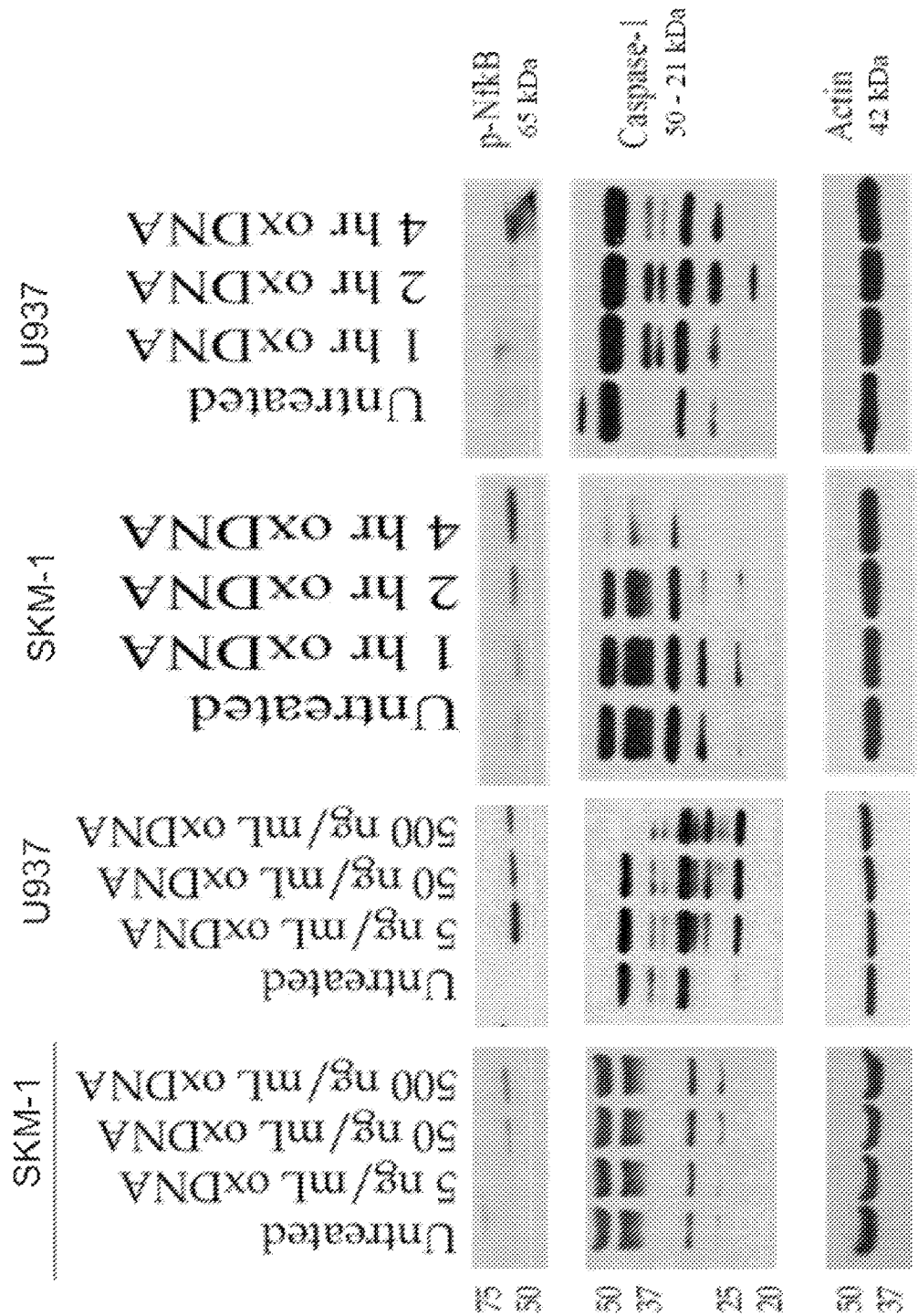

FIGS. 13A to 13E show oxidized-mtDNA as a DAMP in MDS. FIG. 13A shows OxDNA positively correlates with established inflammasome biomarkers and DAMP-activators; ASC specks, S100A9, and S100A8 $p<0.0001$ (Pearson). FIG. 13B shows MDS patients demonstrate significantly higher CXCL10 and ISG15 levels by gene expression array in MDS patients compared to normal donors suggesting increased activation of DNA sensing pathways. FIG. 13C shows Ox-mtDNA treatment of U937 cells results in inflammasome activation, demonstrated by western blot and caspase-1 cleavage. FIG. 13D shows endogenous TLR9 levels in THP-1 (Low), U937 (Med), and SKM-1 (High). FIG. 13E shows SKM-1 and U937 cells are sensitive to ox-mtDNA in a dose, time, and TLR9 expression dependent manner.

Figure 14A:
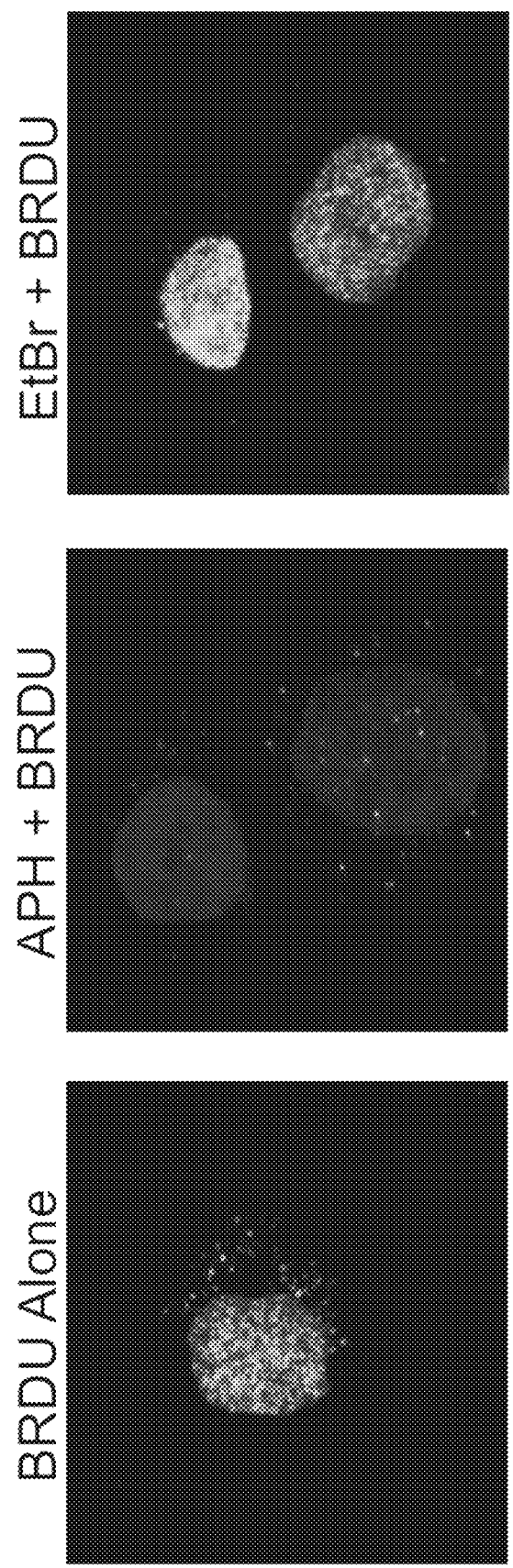
FIGS. 14A to 14E show oxidized-mtDNA interacts with NLRP3. THP-1 cells were incubated with BrdU, aphidicolin (APH, Nuclear DNA Pol α inhibitor), and Ethidium bromide (EtBr, Mitochondrial DNA Pol γ inhibitor) to selectively label Mitochondrial and Nuclear DNA, specificity is demonstrated by IF (FIG. 14A). NLRP3 was immunoprecipitated (IP) and bound DNA was probed for by dot blot which showed that NLRP3 is associated with ox-mtDNA (FIG. 14B).
Figure 14B:
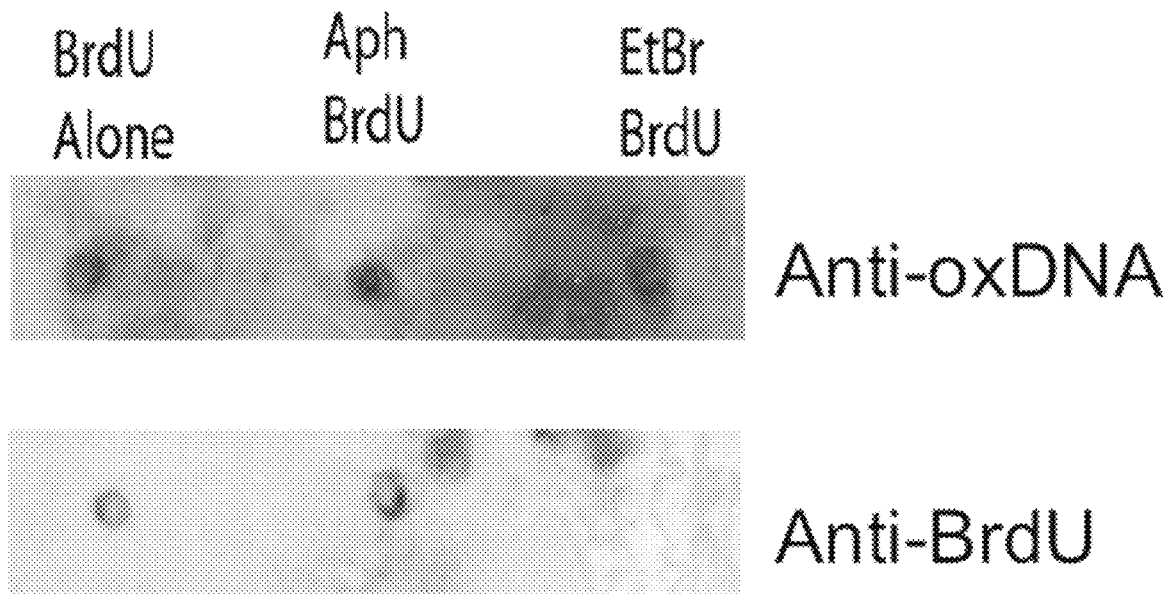
Figure 14C:
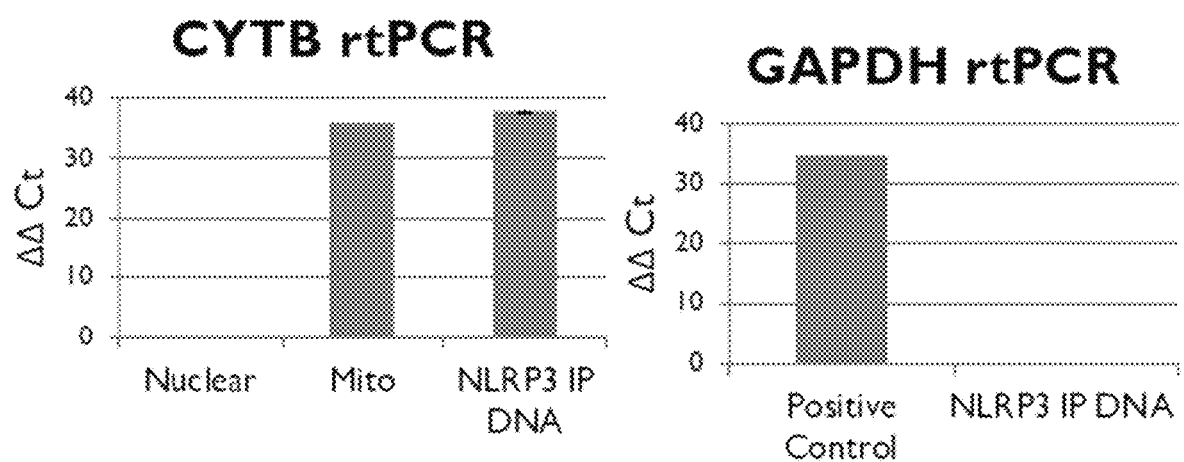
Figure 14D:
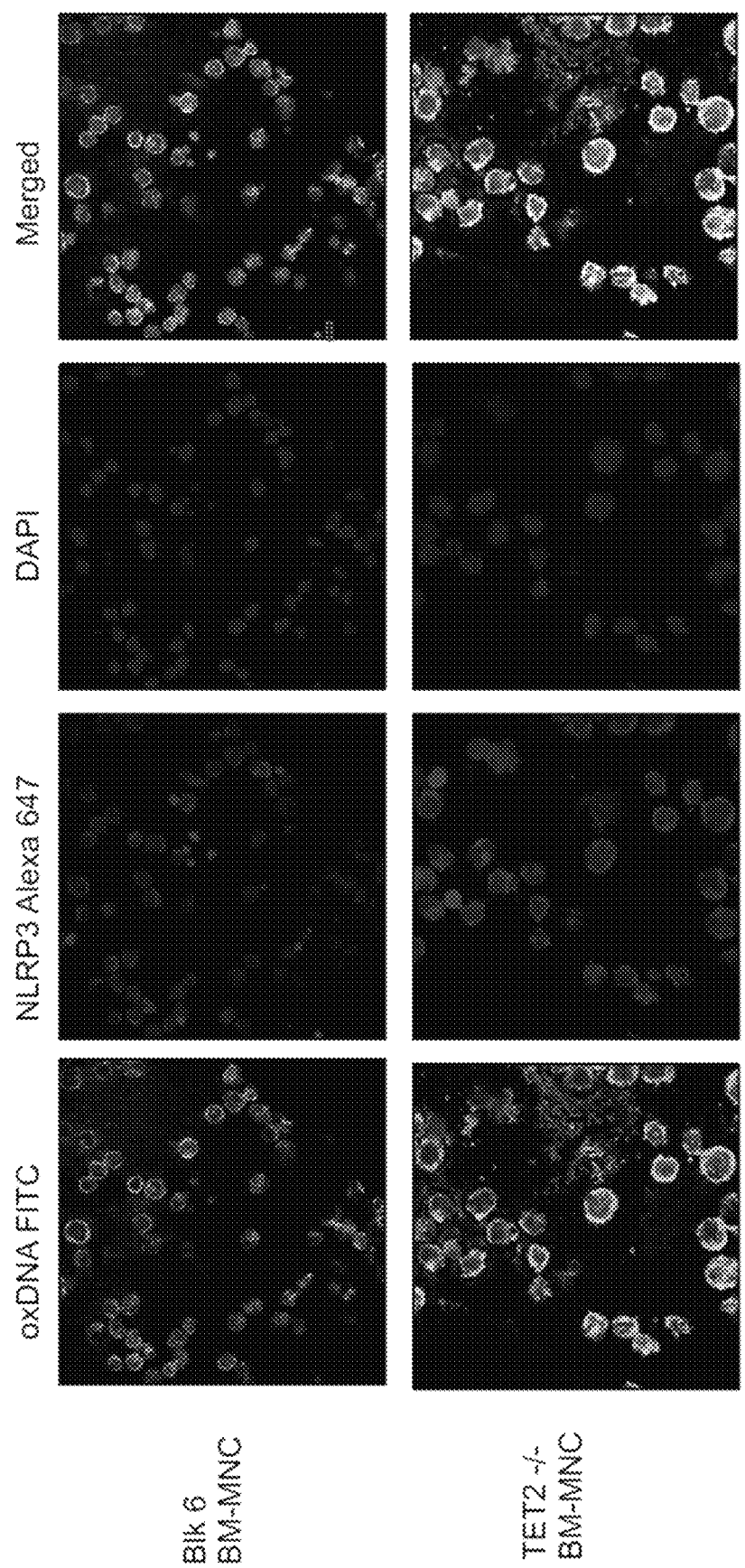
Figure 14E:
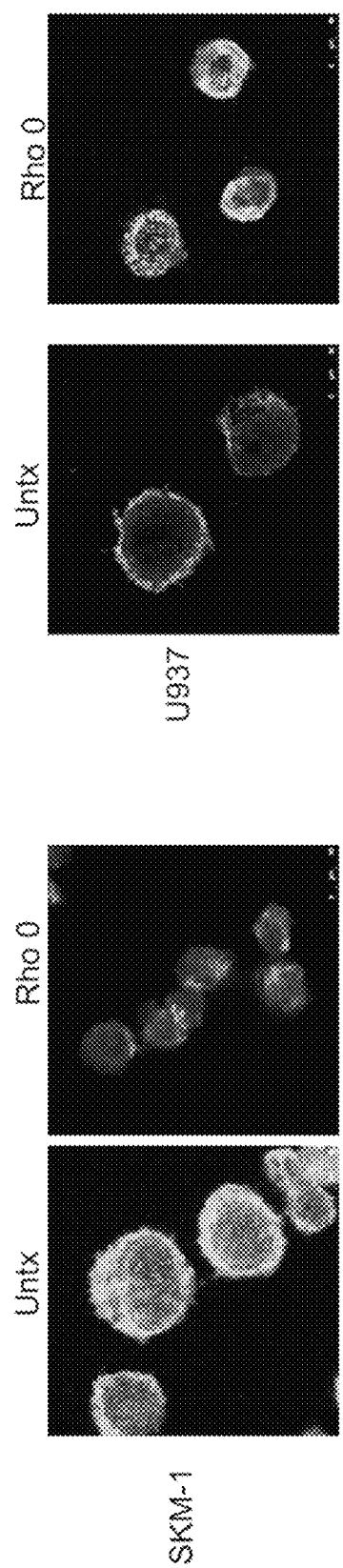

FIGS. 14A to 14E show oxidized-mtDNA interacts with NLRP3. THP-1 cells were incubated with BrdU, aphidicolin (APH, Nuclear DNA Pol α inhibitor), and Ethidium bromide (EtBr, Mitochondrial DNA Pol γ inhibitor) to selectively label Mitochondrial and Nuclear DNA, specificity is demonstrated by IF (FIG. 14A). NLRP3 was immunoprecipitated (IP) and bound DNA was probed for by dot blot which showed that NLRP3 is associated with ox-mtDNA (FIG. 14B). FIG. 14C shows IP NLRP3 probed for mitochondrial genes by PCR. FIG. 14D shows intracellular ox-mtDNA co-localizes with NLRP3 in in driving mutation MDS Murine Models. FIG. 14E shows SKM-1 and U937 cells were cultured for >20 passages in EtBr to deplete mtDNA, these cells will be crucial for future investigations.

Figure 15A:
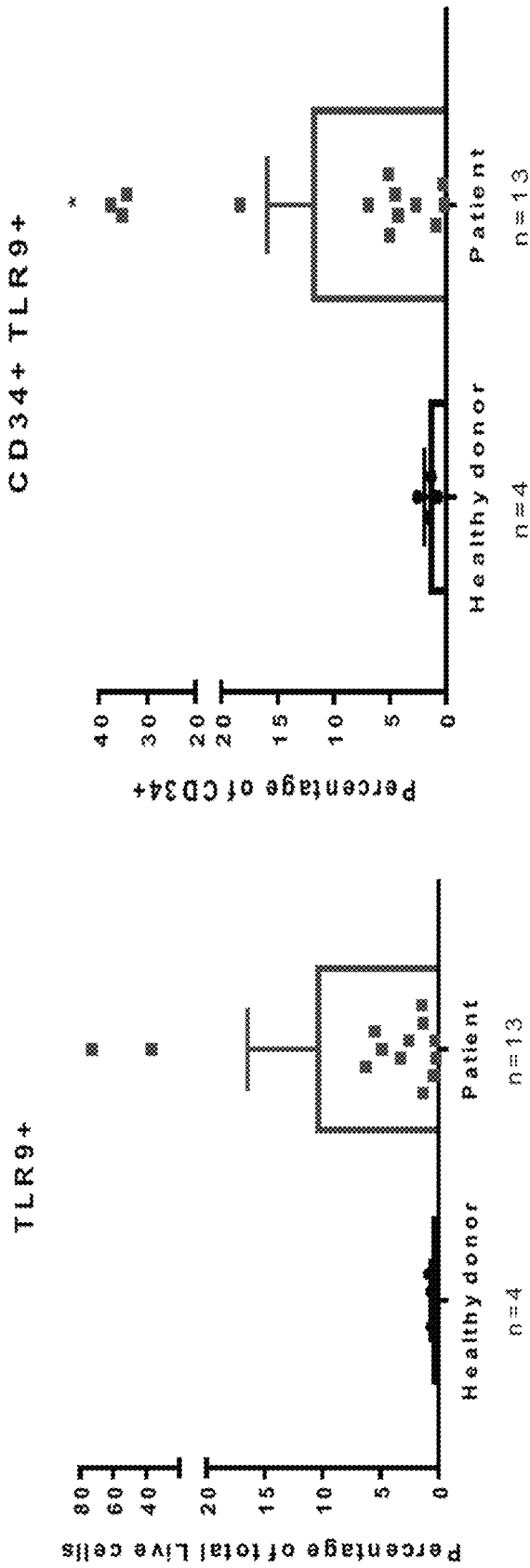
FIGS. 15A to 15G show oxidized-DNA signals via TLR9 & cGAS.
Figure 15B:
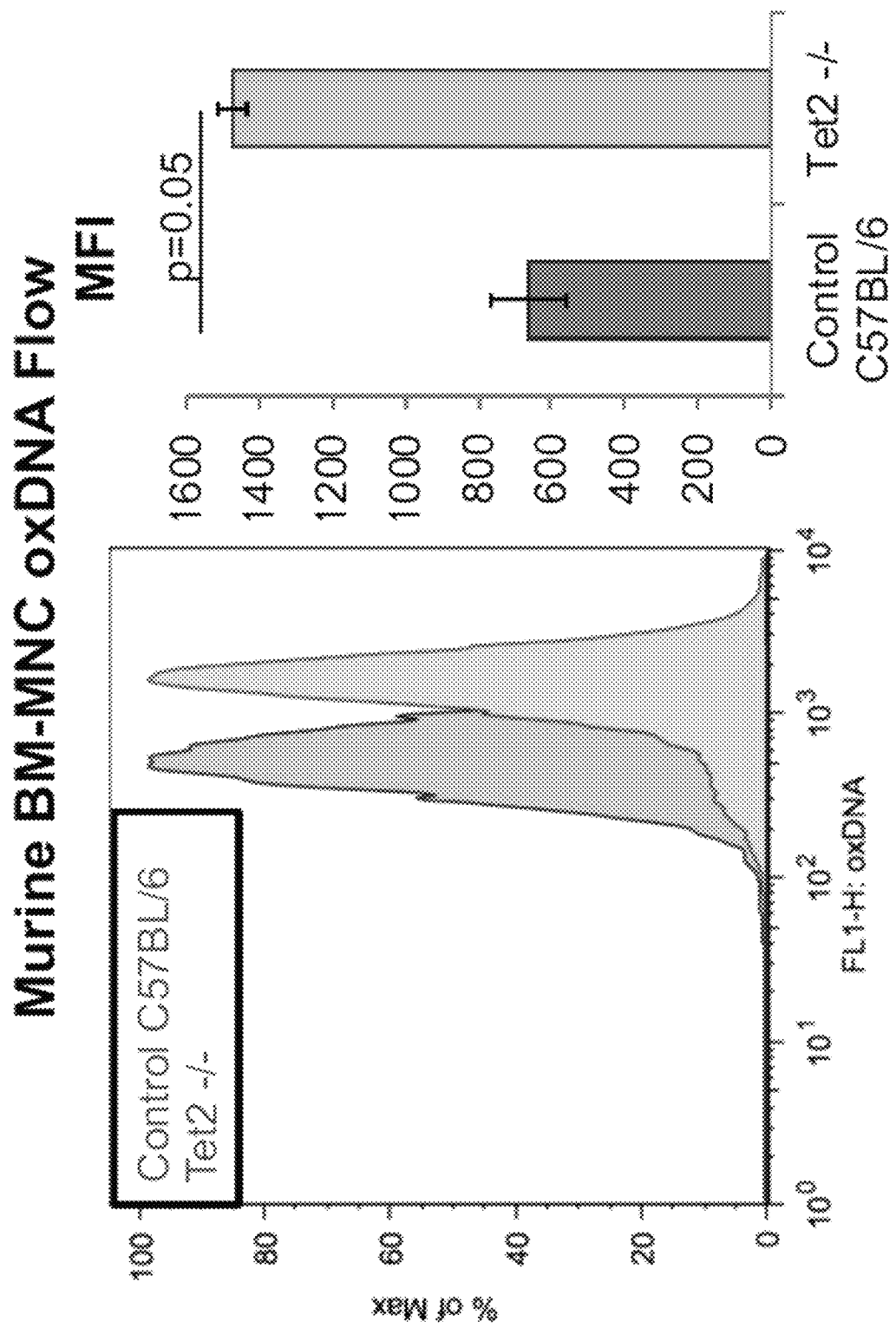
Figure 15C:
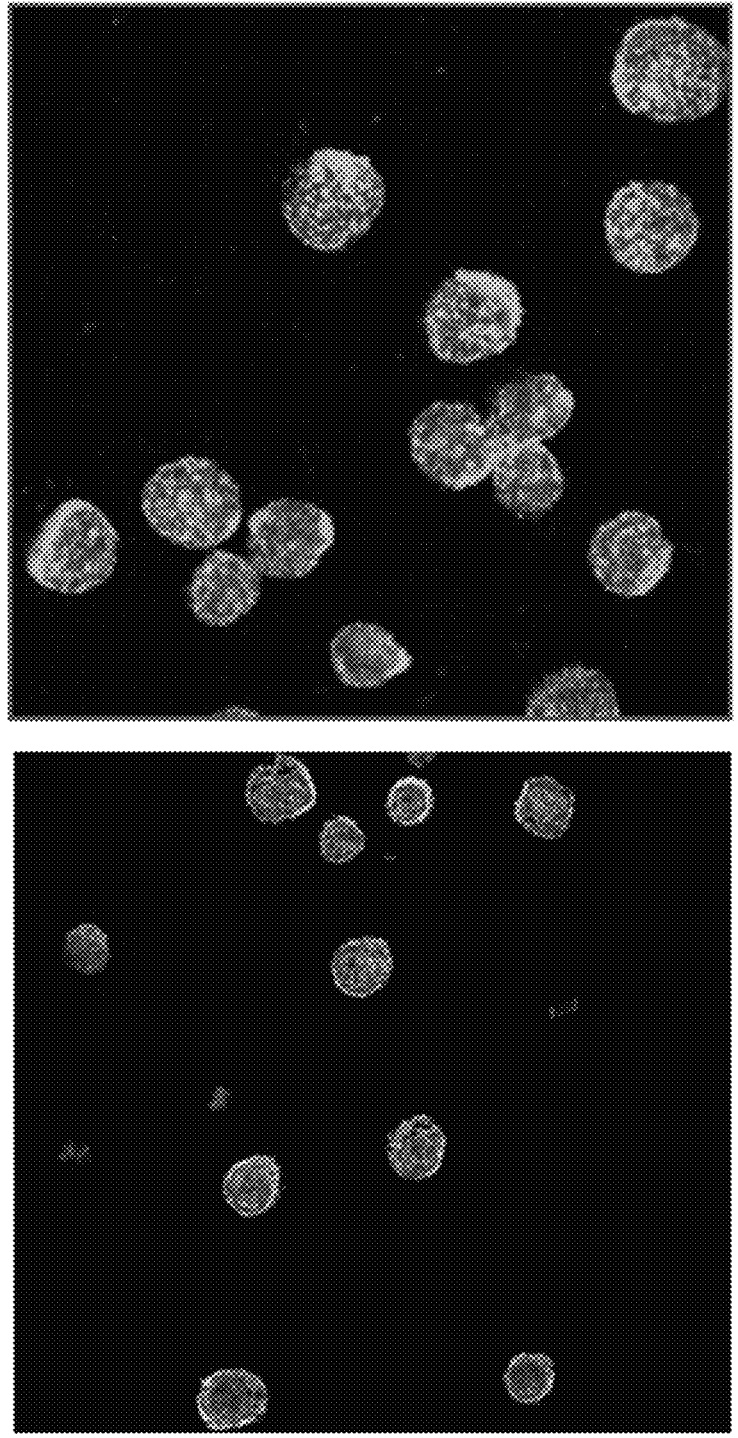
Figure 15D:
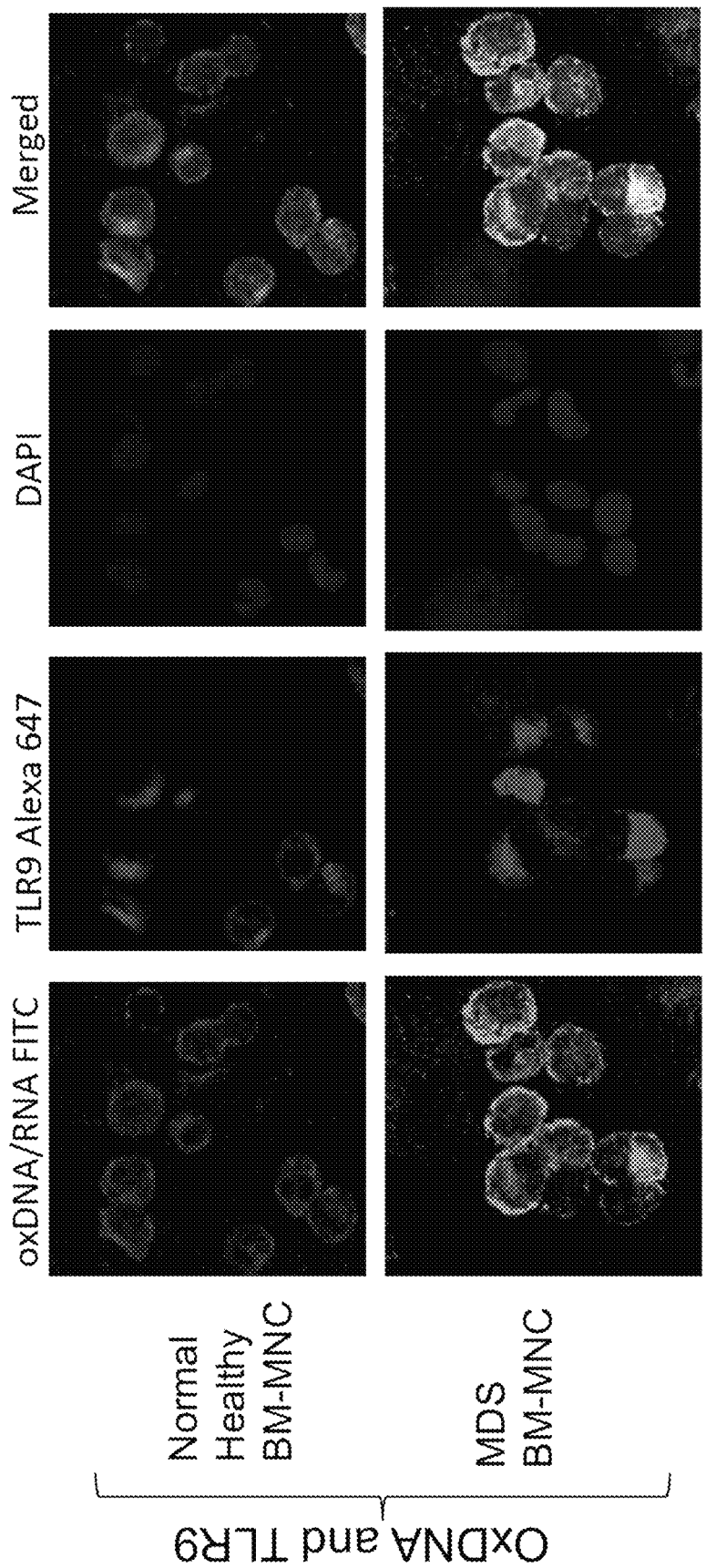
Figure 15E:
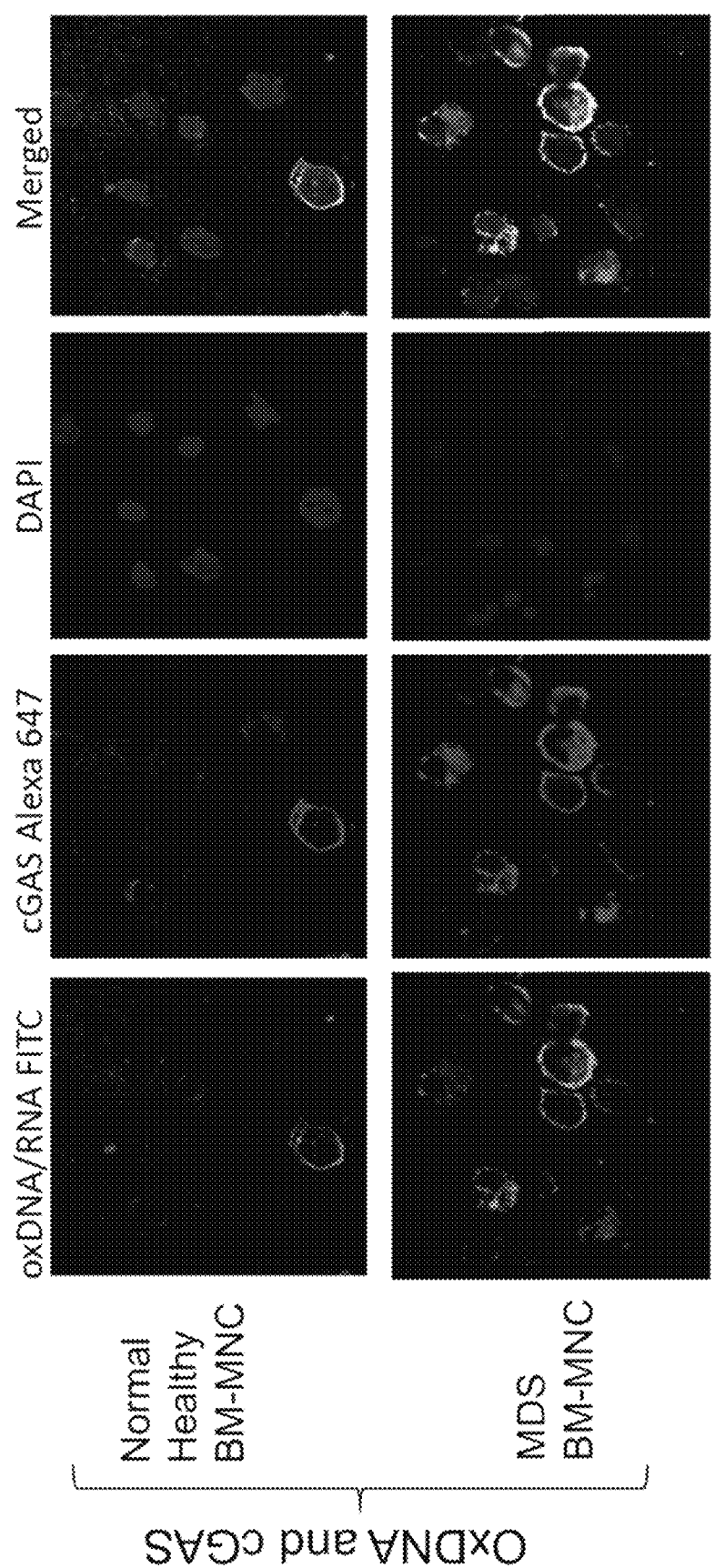
Figure 15F:
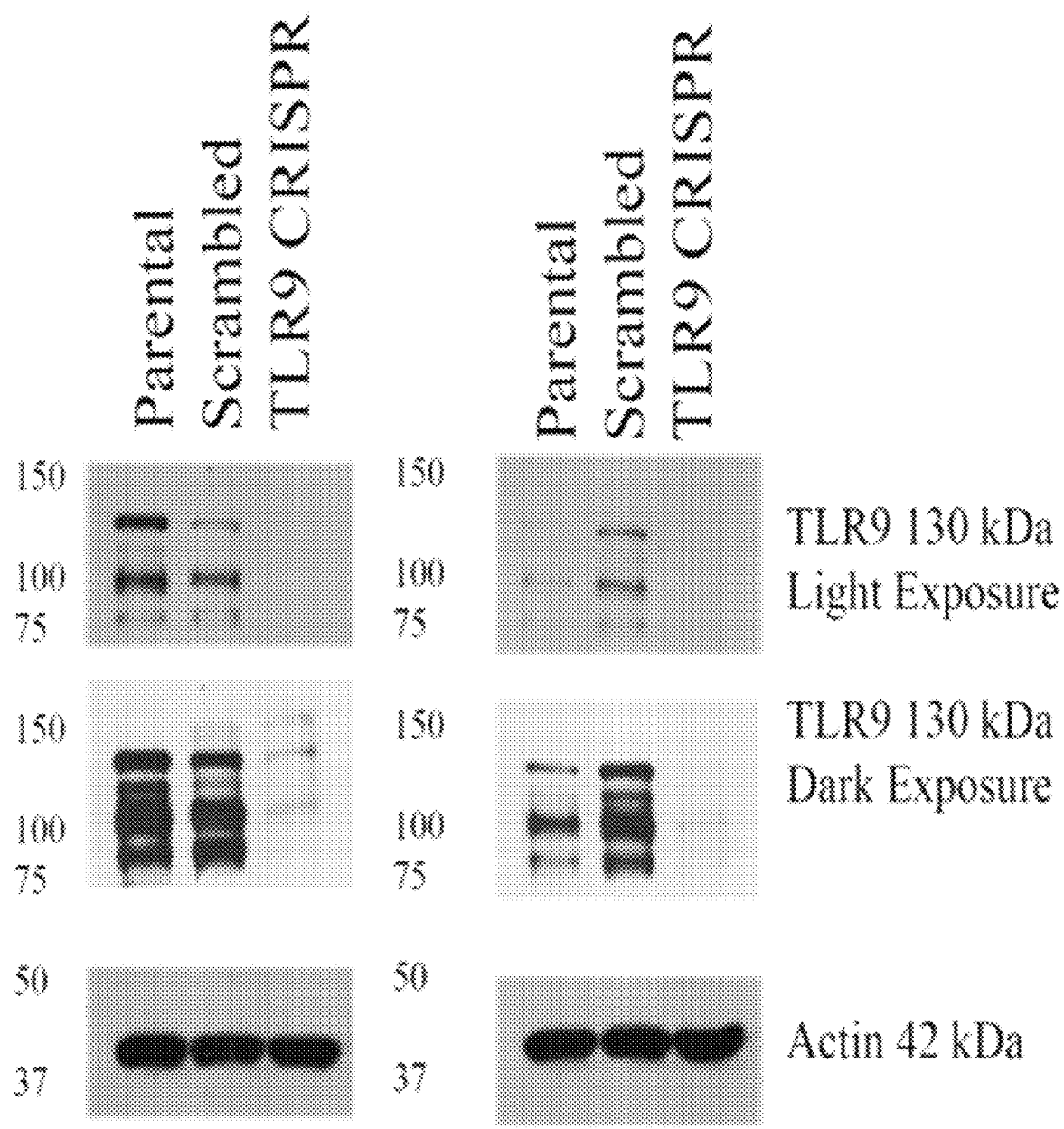
Figure 15G:
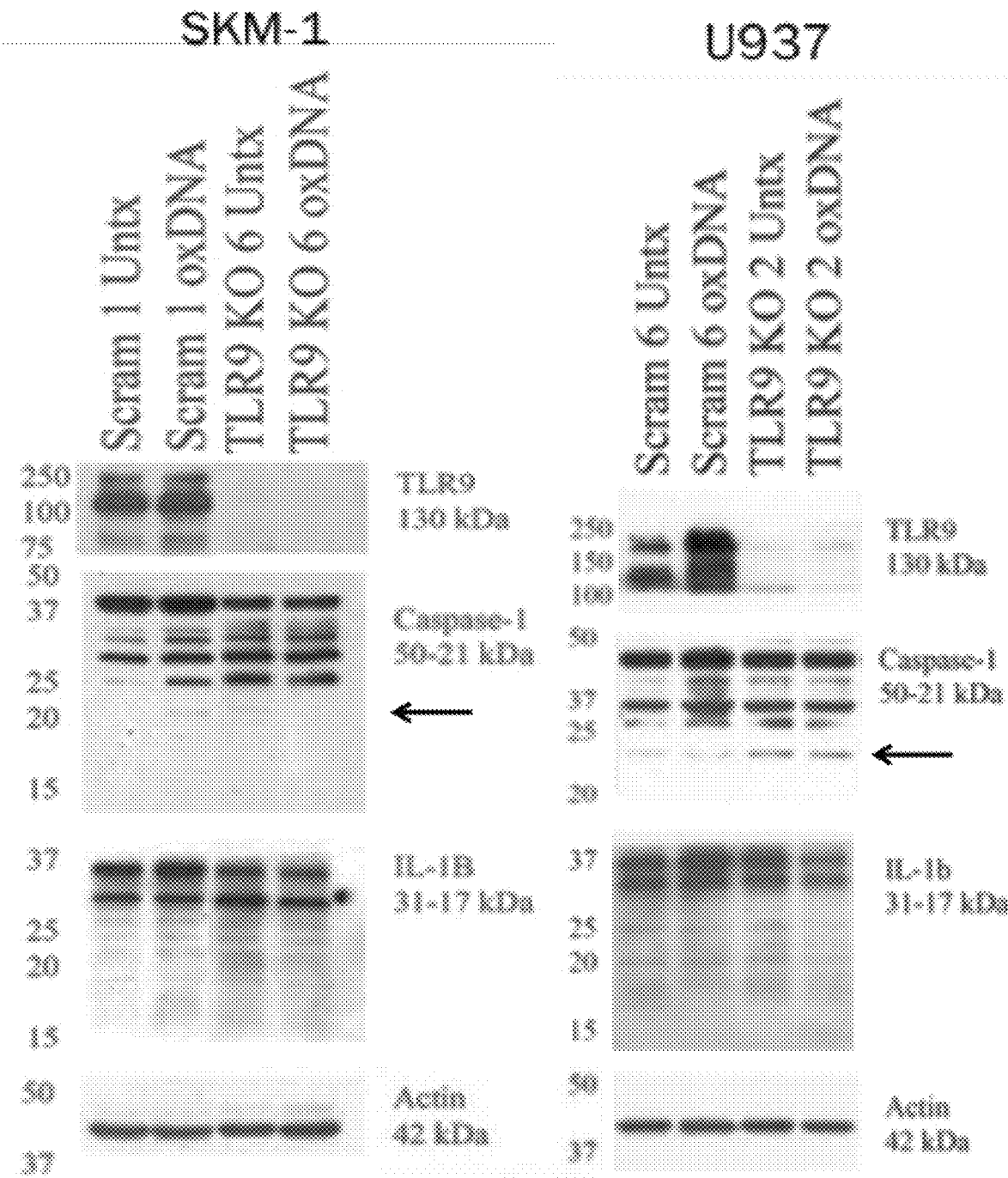

FIGS. 15A to 15G show oxidized-DNA signals via TLR9 & cGAS. FIG. 15A shows TLR9 surface expression is increased in MDS patient mononuclear cells and in particular CD34+ hematopoietic stem cells. FIG. 15B shows OxDNA is significantly increased in a murine model of MDS: Tet2-/- C57BL/6 compared to the wildtype control as shown by flow cytometry (p=0.05). FIG. 15C shows confocal IF imaging demonstrates strong co-localization of TLR9 (Alexa 647) and oxDNA (FITC) in the TET2-/- MDS model. In MDS patient BM-MNC there is increased oxDNA that is strongly co-localized with TLR9 (FIG. 15D) and similarly seen co-localization with cGAS (FIG. 15E) which is not observed in normal BM-MNCs. These results suggest that cGAS and TLR9 pathways may be a mechanism by which oxDNA is recognized to activate the inflammasome. 630×. FIG. 15F shows CRISPR knockout of TLR9 in SKM-1 and U937. FIG. 15G shows TLR9 depleted clones are do not exhibit the same increase cleaved caspase-1 and mature IL-1β in response to oxmtDNA treatment as seen in their scrambled control.

FIG. 16 is an illustration showing MDS hematopoietic stem cells (HSC) inflammasome activation being driven by oxidized mitochondrial DNA through the cGAS-Sting and/or TLR9 pathways. This is followed by pyroptosis and release of ASC specs and oxDNA into the plasma resulting in a feedforward mechanism of inflammasome activation in neighboring HSCs.

CONCLUSIONS

OxDNA is slightly increased in MDS patient bone marrow plasma compared peripheral blood plasma (PB), moving forward PB was assayed. PB oxDNA levels are significantly increased in MDS compared to healthy donors and all other hematologic malignancies except CLL which is previously reported to have oxDNA high levels. OxDNA plasma concentration was significantly higher in LR patients compared to HR patients, consistent with findings that inflammasome activation is highest in LR-MDS. OxDNA demonstrates a strong AUC/ROC score, which highlights its specificity and sensitivity as a biomarker. OxDNA is released as a result of inflammasome activation. OxDNA positively correlates with ASC specks and S100A9/A8 demonstrating the validity of oxDNA as a marker of inflammasome activation. In addition to increased TLR9 surface levels, MDS patients demonstrate significantly higher CXCL10 and ISG15 levels by gene expression array compared to normal donors suggesting increased activation of DNA sensing pathways. Ox-mtDNA is bound to the NLRP3 and activates the inflammasome. Ox-mtDNA treatment results in inflammasome activation, demonstrated by western blot and caspase-1 cleavage. Cell sensitivity sensitive to ox-mtDNA in a dose, time, and TLR9 expression dependent manner. This effect is mitigated by CRISPR knockout of TLR9. In MDS and a MDS murine model cells, there was increased oxDNA which is co-localized with TLR9 and cGAS demonstrating activity of these crucial pathways in inflammasome activation and propagation.

Collectively, these data indicate that ox-mtDNA both directly engages NLRP3 and the DNA sensors TLR9/cGAS to induce IFM activation and pyroptosis, creating a feed forward inflammatory cascade upon cellular release of ox-mtDNA that extends to with neighboring cells. Ox-mtDNA may serve as therapeutic target, a biomarker, and a companion diagnostic for pyroptotic execution in MDS.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A fusion protein, comprising a TLR9 extracellular domain peptide, and an IgG4 Fc domain.

2. The fusion protein of claim 1, defined by the formula:

TLR9-Fc, wherein "TLR9" represents the TLR9 extracellular domain peptide,
wherein "Fc" represents an IgG4 Fc domain, and
wherein "—" represents a linker or hinge domain.

3. The fusion protein of claim 1, wherein the TLR9 extracellular domain comprises the amino acid sequence SEQ ID NO:1, or a variant thereof having at least 90% sequence identity to SEQ ID NO:1.

4. The fusion protein of claim 1, comprising the amino acid sequence SEQ ID NO:7, or a variant thereof having at least 90% sequence identity to SEQ ID NO:7.

5. A composition, comprising the fusion protein of claim 1 in a pharmaceutically acceptable excipient.

6. A method of treating myelodysplastic syndrome (MDS) in a subject, comprising administering to the subject a therapeutically effective amount of a composition of claim 5.

7. The method of claim 6, further comprising detecting in a biological sample from the subject a surrogate marker of pyroptosis to diagnose myelodysplastic syndrome (MDS) in the subject prior to treatment.

8. The method of claim 7, wherein the surrogate marker of pyroptosis comprises oxidized mitochondrial DNA (ox-mtDNA).

9. The method of claim 7, wherein the surrogate marker of pyroptosis comprises apoptosis associated speck-like protein containing a CARD (ASC).

10. The method of claim 7, wherein the biological sample comprises peripheral blood.

* * * * *